(12) United States Patent
Vent

(10) Patent No.: US 12,426,958 B2
(45) Date of Patent: Sep. 30, 2025

(54) NAVIGATED PELVIC IMPLANT SYSTEM AND ASSOCIATED METHOD OF USE

(71) Applicant: GLOBUS MEDICAL, INC., Audubon, PA (US)

(72) Inventor: Justin Vent, Drexel Hill, PA (US)

(73) Assignee: Globus Medical, Inc., Audubon, PA (US)

( * ) Notice: Subject to any disclaimer, the term of this patent is extended or adjusted under 35 U.S.C. 154(b) by 322 days.

(21) Appl. No.: 18/309,307

(22) Filed: Apr. 28, 2023

(65) Prior Publication Data

US 2024/0358443 A1 Oct. 31, 2024

(51) Int. Cl.
| | |
|---|---|
| *A61B 34/20* | (2016.01) |
| *A61B 17/16* | (2006.01) |
| *A61B 17/17* | (2006.01) |
| *A61B 34/32* | (2016.01) |
| *G16H 20/40* | (2018.01) |
| *A61B 17/56* | (2006.01) |
| *A61B 34/10* | (2016.01) |
| *A61B 90/00* | (2016.01) |

(52) U.S. Cl.
CPC .......... *A61B 34/20* (2016.02); *A61B 17/1664* (2013.01); *A61B 17/1703* (2013.01); *A61B 17/1742* (2013.01); *A61B 34/32* (2016.02); *G16H 20/40* (2018.01); *A61B 2017/564* (2013.01); *A61B 2034/107* (2016.02); *A61B 2034/108* (2016.02); *A61B 2090/3762* (2016.02)

(58) Field of Classification Search
CPC ......... A61B 34/20; A61B 34/32; A61B 17/17; A61B 17/1703; A61B 17/1742; A61B 17/16; A61B 17/1664; G16H 20/40
See application file for complete search history.

(56) References Cited

U.S. PATENT DOCUMENTS

| | | | | |
|---|---|---|---|---|
| 8,709,016 | B2 * | 4/2014 | Park | A61B 90/13 |
| | | | | 606/91 |
| 9,339,277 | B2 * | 5/2016 | Jansen | A61B 34/20 |
| 11,298,189 | B2 * | 4/2022 | Kelman | A61B 34/10 |

* cited by examiner

*Primary Examiner* — Christopher J Beccia

(57) ABSTRACT

A navigated pelvic implant system includes a robot with a control unit and an end effector, at least one patient position sensor in electronic communication with the robot, and a database of anatomical information, including anatomical features, that is in electronic communication with the control unit; where the control unit receives patient imaging information and determines variance between a patient and other patients found in the database, and then the control unit selects at least one implant and an associated trajectory for surgery, then the control unit determines position of the patient through input imaging data and input from the at least one patient position sensor, the control unit will then proceed with the previously determined implant and trajectory, followed by the end effector using a drill to create an opening and holding an implant insertion mechanism to secure the implant within the opening in the patient's pelvis.

20 Claims, 28 Drawing Sheets

| Classification | Severity | | |
|---|---|---|---|
| Anterior Posterior Compression (APC) | APC1 | APC2 | APC3 |
| APC Trajectory Selection | Pubic Symphysis (PS) | Pubic Symphysis (PS), Iliosacral (IS), Transacral (TS) | Pubic Symphysis (PS) Iliosacral (IS), Transacral (TS) |
| Lateral Compression (LC) | LC1 | LC2 | LC3 |
| LC Trajectory Selection | Anterior Column (AC), Posterior Column (PC), Iliosacral (IS) | Anterior Column (AC) Posterior Column (PC), Iliosacral (IS), Lateral Compression (LC2) | Anterior Column (AC), Posterior Column (PC), Iliosacral (IS), Transacral (TS), Lateral Compression (LC2) |
| Vertical Shear (VS) | VS | | |
| VS Trajectory Selection | Anterior Column (AC), Posterior Column (PC) Iliosacral (IS), Transacral (TS) | | |

FIG. 6

NAVIGATED PELVIC IMPLANT SYSTEM AND ASSOCIATED METHOD OF USE

FIELD OF THE INVENTION

The present invention generally relates to a navigated pelvic implant system and associated method to treat fractures of a patient's pelvic region.

BACKGROUND OF THE INVENTION

The background description provided herein gives context for the present disclosure. Work of the presently named inventors, as well as aspects of the description that may not otherwise qualify as prior art at the time of filing, are neither expressly nor impliedly admitted as prior art.

Fractures of the pelvic ring, or trauma fractures, are the leading cause of death of patients between the ages of fifteen and twenty-four and account for thirty percent of all intensive care unit ("ICU") visits annually. These fractures are usually high-energy fractures and/or high-impact events from car accidents, crush accidents, or falling from a significant height. However, these fractures can also occur in patients with bone-weakening diseases such as osteoporosis, and diabetes, or can occur due to an athletic injury.

A fracture in one part of the pelvis is often accompanied by a fracture or damage to ligaments at another point due to the pelvis's ring-like structure. Pelvic fractures are also described as "stable" or "unstable" based on how much damage has occurred to the structural integrity of the pelvis. Stable fractures typically are a singular break in the pelvic ring, and broken ends of the bones line up, whereas unstable fractures are two or more breaks in the pelvic ring, and the broken pieces are displaced. Many surgeons use multiple classification systems and imaging modalities such as AP pelvis radiographs, CT scans, and stress radiographs when developing treatment plans and planning surgical interventions.

There are two different classifications of pelvic fractures: the Young-Burgess classification and the Tile classification. According to the Young-Burgess Classification system, pelvic disruptions are divided into Anterior Posterior Compression (APC), Lateral Compression (LC), Vertical Shear (VS), and Combined Mechanism (CM) categories where LC and APC have subsets based on the increasing severity of the injury produced by increasing the magnitude of the force. This classification is based on the stability of the pelvis and on the mechanism of injury and serves as the AO Foundation/Orthopaedic Trauma Association ("AO/OTA") fracture classification. This classification uses the concept of pelvic ring stability to differentiate injuries into three primary categories, each with subsets of injury patterns. Type A injuries are stable and do not disrupt the pelvic ring; type B injuries are vertically stable but rotationally unstable, while Type C injuries are vertically and rotationally unstable.

There are three main surgical fixation options for pelvic fractures. This includes External Fixation, Open Reduction Internal Fixation (ORIF), and Percutaneous Fixation. All three of these fixation options depend on the patient's fracture pattern and severity, the severity of other injuries, patient/surgeon/hospital (operating room) availability, and other patient comorbidities.

External Fixation can be used for pelvic fractures as a temporary fixation option or definitive treatment, which is rare and typically only if the surgeon cannot use Open Reduction Internal Fixation (ORIF) on the pelvis. However, careful placement of associated implant instruments is needed, which requires significant fluoroscopic guidance. In addition, this External Fixation process provides additional time to the surgery, increases radiation to patient and operating room staff, and increases the risk of infection.

Open Reduction Internal Fixation (ORIF) is where the pelvic bones are rigidly fixed with plates and screws to prevent future displacement of the bones/joints and allow patient rehabilitation quicker. Some of the disadvantages of ORIF include difficult visualization of the fracture due to soft tissue, nerves and/or ligaments and the deep structure of the pelvis, difficulty in obtaining reduction, need for multiple surgeons, high usage of fluoroscopy for implantation, and potential patient problems of wound healing, damage to major vessels or nerves and increased incidence of infection.

Finally, Percutaneous Fixation is a type of fixation that is a less invasive alternative fixation method that is a safe, reproducible method that is biomechanically stable with reduced blood loss and infection. This technique may offer a shorter surgical time, reduce exposure-related hazards and decrease soft-tissue disruption. The disadvantages of this fixation are that high usage of fluoroscopy is needed. Since this is a minimally invasive surgery ("MIS"), surgeons must recognize the adjacent organs found within and around the pelvis and must comprehend and recognize the specific safe zones of screw insertion. The most common complications with this fixation are nerve root injury, screw misplacement, and loss of reduction Thus, there is a need in the art for a navigated procedure that will provide safe and reliable fracture reduction, safe and accurate screw trajectory, navigated percutaneous screw preparation and insertion and/or placement, and reduce overall radiation and blood loss and operating time.

SUMMARY OF THE INVENTION

The following objects, features, advantages, aspects, and/or embodiments are not exhaustive and do not limit the overall disclosure. No single embodiment needs to provide each and every object, feature, or advantage. Any of the objects, features, advantages, aspects, and/or embodiments disclosed herein can be integrated with one another, either in full or in part.

It is a primary object, feature, and/or advantage of the present invention to improve on or overcome the deficiencies in the art.

It is an aspect of the present invention to have a system that includes a robot having a control unit having at least one processor, and an end effector, at least one patient position sensor in electronic communication with the robot, and a database of anatomical information, including anatomical features, that is in electronic communication with the control unit, where the control unit receives patient imaging information and determines variance between a patient and other patients found in the database of anatomical information, and then the control unit selects at least one implant and an associated trajectory for surgery, then the control unit determines position of the patient through input imaging data and input from the at least one patient position sensor, the control unit will then proceed with the previously determined implant and trajectory, unless alteration is required, which is followed by the end effector selectively holding a drill to create an opening in a patient's pelvis along the trajectory that is then followed by the end effector selectively holding an implant insertion mechanism to secure the implant within the opening in the patient's pelvis.

It is another aspect of the system of the present invention that the implant insertion mechanism is a driver array, and the implant is a screw.

It is another aspect of the system of the present invention to utilize a database of anatomical information that includes fracture patterns and fracture level severity to compare a patient against a larger group of patients.

It is still another feature of the system of the present invention to determine the position of the patient with a CT scan with at least one reference device selected from the group consisting of a surveillance marker, a bone anchor, a dynamic reference base array, interoperative CT registration fixture, and a fluoro fixture.

It is still another aspect of the system of the present invention to determine the position of the patient with a CT scan with at least two reference devices selected from the group consisting of a surveillance marker, a bone anchor, a dynamic reference base array, an interoperative CT registration fixture, and a fluoro fixture.

Yet another aspect of the system of the present invention involves utilizing a soft tissue sleeve and trocar with the end effector of the robot to perform soft tissue dilation prior to drilling, Still, yet another feature of the system of the present invention involves utilizing at least one cannula with the end effector of the robot to perform soft tissue dilation prior to drilling, Another feature of the system of the present invention involves inserting wire with an end effector of the robot followed by removal of the at least one cannula prior to placement of an implant insertion mechanism to secure an implant in a patient's pelvis.

Still another aspect of the system of the present invention is a drill array that includes a threaded sleeve having a geometrically shaped end portion for engagement into a screw.

A further feature of the system of the present invention includes a geometrically shaped end portion of the driver array that is hexalobular.

Yet another feature of the method of the present invention is a drill array that includes a collet sleeve positioned over a collet securing a geometrically shaped end portion for engagement into a screw, It is still another feature of the system of the present invention is a screw that includes a threaded connection and a geometrically shaped top portion.

In still yet another aspect of the system of the present invention is a screw having a geometrically shaped top portion that is hexalobular.

It is yet a further aspect of the system of the present invention is a screw that includes bone interlocking geometry with an undercut on both the top and bottom of the flutes of the screw, Still, yet another feature of the system of the present invention includes a captured washer utilized with the screw, where the captured washer includes flexural grooves to secure the screw.

Another feature of the system of the present invention is a navigated pelvic implant system that includes a robot having a control unit having at least one processor, and an end effector, at least one patient position sensor in electronic communication with the robot, and a database of anatomical information, including anatomical features, that is in electronic communication with the control unit; where the control unit receives patient imaging information and determines variance between a patient and other patients found in the database of anatomical information, then the control unit selects at least one screw and an associated trajectory for surgery, then the control unit determines position of the patient through input imaging data and input from the at least one patient position sensor, the control unit will then proceed with the previously determined screw and trajectory after verification by the control unit, unless alteration is required, which is followed by the end effector selectively holding a drill to create an opening in a patient's pelvis along the trajectory that is then followed by the end effector selectively holding a driver that secures the screw within the opening in the patient's pelvis in accordance with reduction techniques followed by the control system providing surgical procedure verification and providing input into the control system for adjustments to the surgical procedure.

It is an aspect of the system of the present invention that includes inputting patient procedure and pain information into the control system after the surgical procedure.

It is another aspect of the present invention to have a method for providing navigated pelvic implants that includes receiving patient imaging information and determining variance between a patient and other patients in a database of anatomical information, including anatomical features, that is in electronic communication with a control unit, having at least one processor, for a robot having an end effector, selecting at least one implant and an associated trajectory for surgery with the control unit, determining a position of a patient through input imaging data and input from at least one patient position sensor in electronic communication with the control unit, implementing the previously selected implant and trajectory, unless alteration is required, selectively holding a drill to create an opening in the patient's pelvis along the trajectory with the end effector, and selectively holding an implant insertion mechanism to secure the implant within the opening in the patient's pelvis with the end effector.

Still, another feature of the method of the present invention includes that the implant insertion mechanism is a driver array, and the implant is a screw.

Still, another aspect of the method of the present invention includes utilizing at least one cannula with the end effector of the robot to perform soft tissue dilation prior to drilling and inserting wire with the end effector of the robot, followed by removal of the at least one cannula prior to placement of an implant insertion mechanism to secure an implant in a patient's pelvis.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

Several embodiments in which the present invention can be practiced are illustrated and described in detail, wherein like reference characters represent like components throughout the several views. The drawings are presented for exemplary purposes and may not be to scale unless otherwise indicated.

FIG. 6 is a table of pelvic fracture classifications and associated severities.

An artisan of ordinary skill in the art need not view, within the isolated figure(s), the nearly infinite number of distinct permutations of features described in the following detailed description to facilitate an understanding of the present invention.

DETAILED DESCRIPTION OF THE INVENTION

The present disclosure is not to be limited to that described herein. Mechanical, electrical, chemical, procedural, and/or other changes can be made without departing from the spirit and scope of the present invention. Unless otherwise indicated, no features shown or described are essential to permit the basic operation of the present invention.

Figure 1:
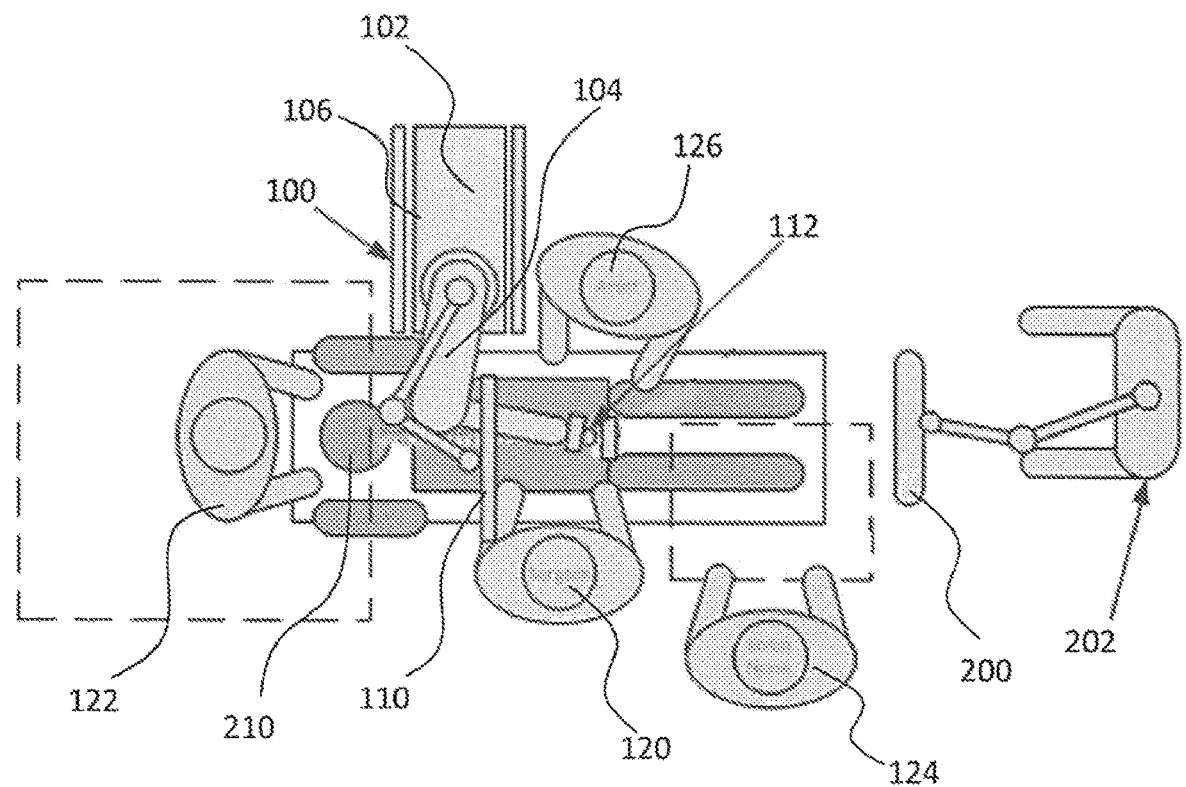
FIG. 1 shows a top view of a robotic surgical system for implementing the present invention.
Figure 2:
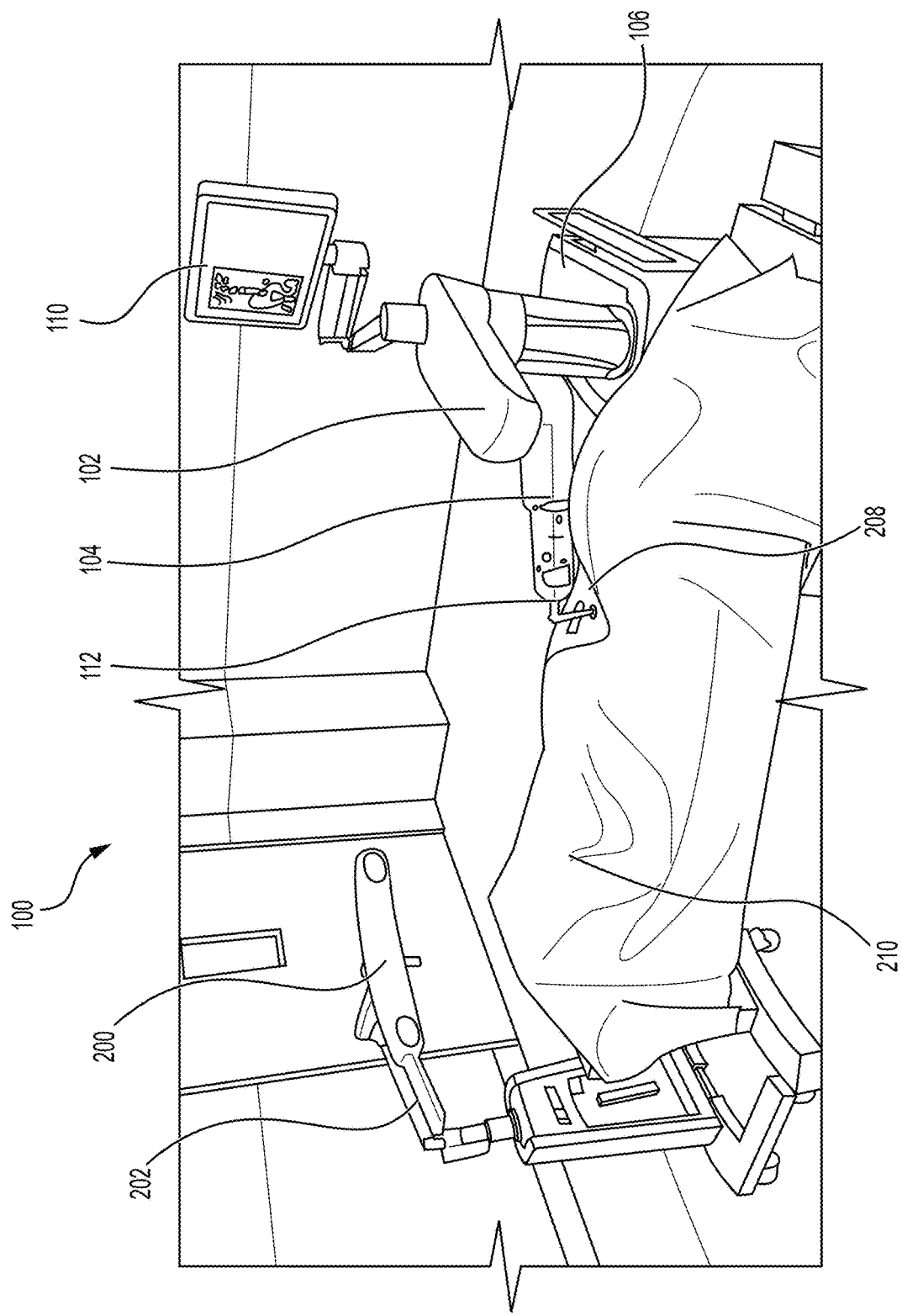
FIG. 2 is a perspective view of the robotic surgical system for implementing the present invention shown in FIG. 1

Turning now to the drawings, FIGS. 1 and 2 illustrate a surgical robot system 100 in accordance with an exemplary embodiment. Surgical robot system 100 may include, for example, a surgical robot 102, one or more robot arms 104, a base 106, a display 110, and an end effector 112. An illustrative, but nonlimiting, example of surgical robotic systems that can be adapted to the present invention includes the Excelsius™ platform, which contains Excelsius GPS®, Excelsius3D™, Excelsius Hub™, Excelsius XR™, and Excelsius Flex™ which are all manufactured by Globus Medical Inc. having a place of business at 2560 General Armistead Ave Audubon, Pennsylvania 19403. In addition, a wide variety of other surgical robotic systems can suffice that have accurate positioning and control of the end effector for a robot.

For example, the surgical robot system 100 may also utilize a camera 200 positioned on a camera stand 202. The camera stand 202 can have any suitable configuration to move, orient, and support the camera 200 in a desired position. In addition, the camera 200 may include any suitable camera or cameras, such as one or more infrared cameras (e.g., bifocal or stereophotogrammetric cameras). Moreover, a potential configuration for the placement of the surgical robot system 100 in an operating room environment is also shown in FIGS. 1 and 2. For example, robot 102 may be positioned near or next to patient 210. Although depicted near the head of patient 210, it will be appreciated that robot 102 can be positioned at any suitable location near patient 210, depending on the pelvic area of patient 210 undergoing the surgical operation. Numerous types of patient positional sensors for the patient may be utilized with the present invention, with the camera only being an illustrative, but nonlimiting, example.

The camera 200 may be separated from the robotic system 100 and positioned at the foot of patient 210. This location allows camera 200 to have a direct visual line of sight to the surgical field 208, as shown in FIG. 2. Again, it is contemplated that the camera 200 may be located at any suitable position having a line of sight to the surgical field 208. In the configuration shown, the surgeon 120 may be positioned across from the robot 102 but is still able to manipulate the end-effector 112 and the display 110. A surgical assistant 126 may be positioned across from the surgeon 120 again with access to both the end-effector 112 and the display 110. If desired, the locations of surgeon 120 and assistant 126 may be reversed. The traditional areas for the anesthesiologist 122 and the nurse or scrub tech 124 remain unimpeded by the locations of the robot 102 and camera 200.

With respect to the other components of the surgical robot 102, display 110 can be attached to the surgical robot 102, and in other exemplary embodiments, display 110 can be detached from the surgical robot 102, either within a surgical room with surgical robot 102 or in a remote location. In addition, end-effector 112 may be coupled to the robot arm 104 and controlled by at least one motor.

The surgical robot 102 is able to control the translation and orientation of the end-effector 112. Robot 102 is able to move end-effector 112 along the x, y, and z-axes. In addition, the end-effector 112 can be configured for selective rotation about one or more of the x, y, and z-axis, as well as a Z Frame axis such that one or more of the Euler Angles, e.g., roll, pitch, and/or yaw, associated with end-effector 112 can be selectively controlled. In some situations, selective control of the translation and orientation of end-effector 112 can permit the performance of medical procedures with significantly improved accuracy compared to conventional robots that utilize, for example, a six-degree-of-freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the end effector 112 can be dynamically updated so that surgical robot 102 can be aware of the location of the end effector 112 at all times during the surgical procedure.

The first step in the workflow process is to bring the surgical robotic system 100 into an operating room, along will all implants and instruments needed for the surgery, and electrical power will be applied to the surgical robotic system 100. If medical images and/or patient scans are required for the procedure and are not in the system associated with the medical facility, they can be downloaded from various sources. These include, but are not limited to, CD/DVD, USB, or a medical facility's picture archiving and communication system, i.e., PACS. If medical images and/or scans of the patient are already located in the medical facilities' system, then the plan for the procedure can then be downloaded from a cloud resource (preferably associated with the supplier of the surgical robotic system 100) or a portable USB storage. A technical specialist of the healthcare facility, e.g., a scrub technologist 124 or a technical specialist from the supplier of the surgical robotic system 100, can then ensure that the surgical robotic system 100 is set up correctly and is ready for use.

In addition, the surgical robotic system 100 includes the natural anatomic pelvis complexity and the injury's severity for robotically enabled pelvic screw fixation. There is a database in which volunteered patients, or cadaveric specimens are imaged to provide the database with anatomical data. This data is processed by a processor in which key anatomical landmarks and characteristics are measured. As this data is continuously entered into the database, machine learning processes this information and segments the data into various patient groups based on age, sex, ethnicity, BMI, and measurements of anatomical landmarks and characteristics. This data will then provide the system with an average of those measured anatomical landmarks and characteristics, based on those segmented patient groups.

Figure 3:
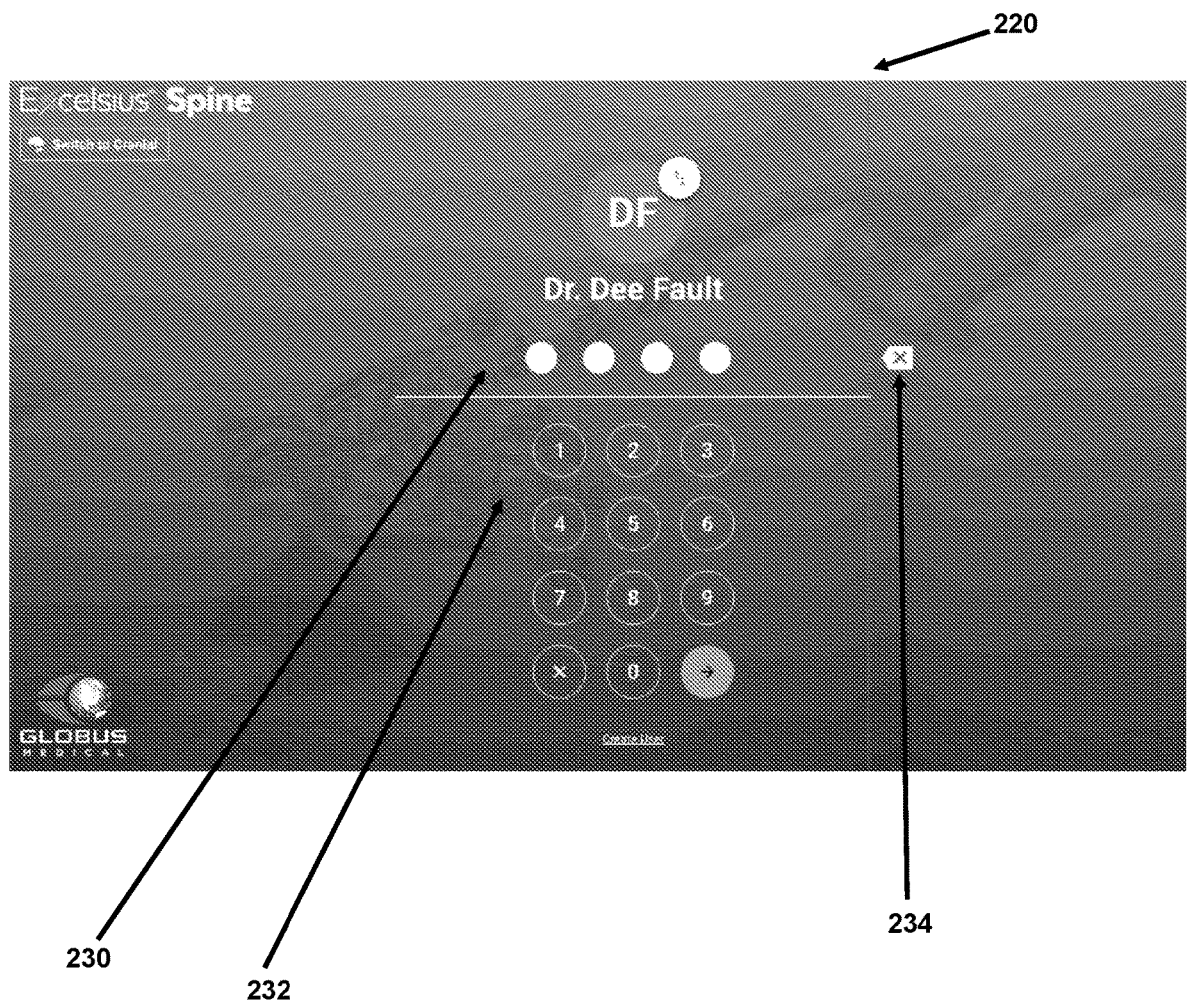
FIG. 3 is a front view of a login screen associated with the robotic surgical system for the present invention.

Referring now to FIG. 3, an illustrative but nonlimiting, login screen for the technical specialist of the healthcare facility, e.g., scrub technologist 124 from FIG. 1, or a technical specialist from the supplier of the surgical robotic system 100, is generally indicated by numeral 220. This includes a place to enter login information 230, a touchpad to type in login information 232, and a cancel function 234. Any of a wide variety of electronic displays can be utilized, including tablets and other portable devices.

Figure 4:
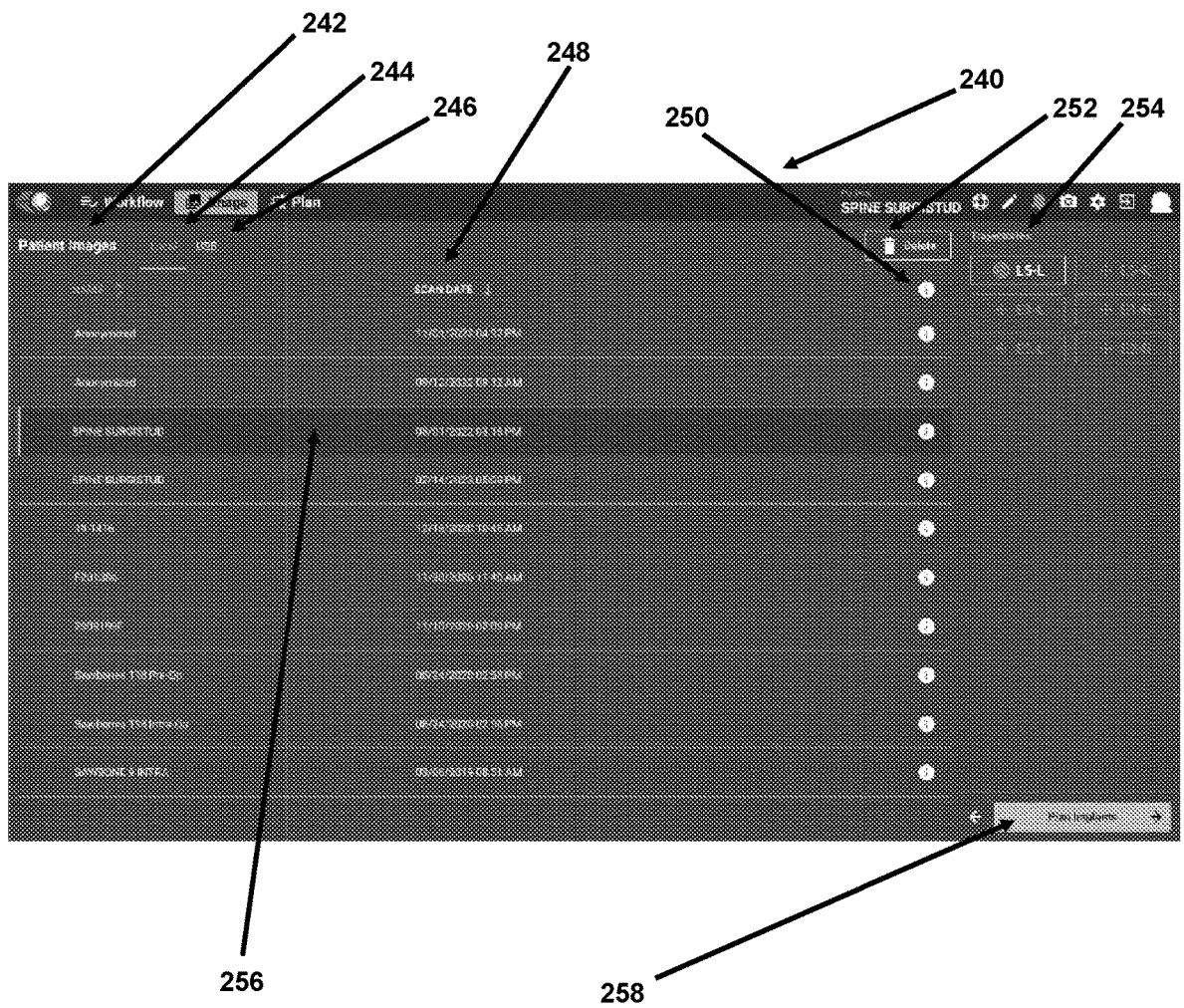
FIG. 4 is a front view of a patient information selection electronic display screen associated with the present invention.

The next step is to select the appropriate patient information on the screen shown in FIG. 4, which is generally indicated by the numeral 240, which a surgeon typically performs. A listing of medical image files is generally indicated by the numeral 242. There is a first indicator from files from a first source 244, e.g., local, and files from a second source 246, e.g., USB. Next, there is a column of dates and times of scanning of the medical image files 248 that correlates to the column of medical image files 242. In addition, there is a third column of information icons 250 that correlates to the column of dates and times of scanning of the medical image files 248 and the column of medical image files 242 to click by the user to provide additional information regarding each medical image file 248.

There is a delete function 252 to remove unwanted or outdated medical image files 248. When a particular medical image file 242, scan date and time 248, and information icon 250 are selected, as indicated by the numeral 256, the associated trajectory, including a left or right designation, is indicated by the outputs shown in numeral 254. Finally, there is an input button 258 that allows the user to proceed to the next screen and plan the implant procedure.

Figure 5:
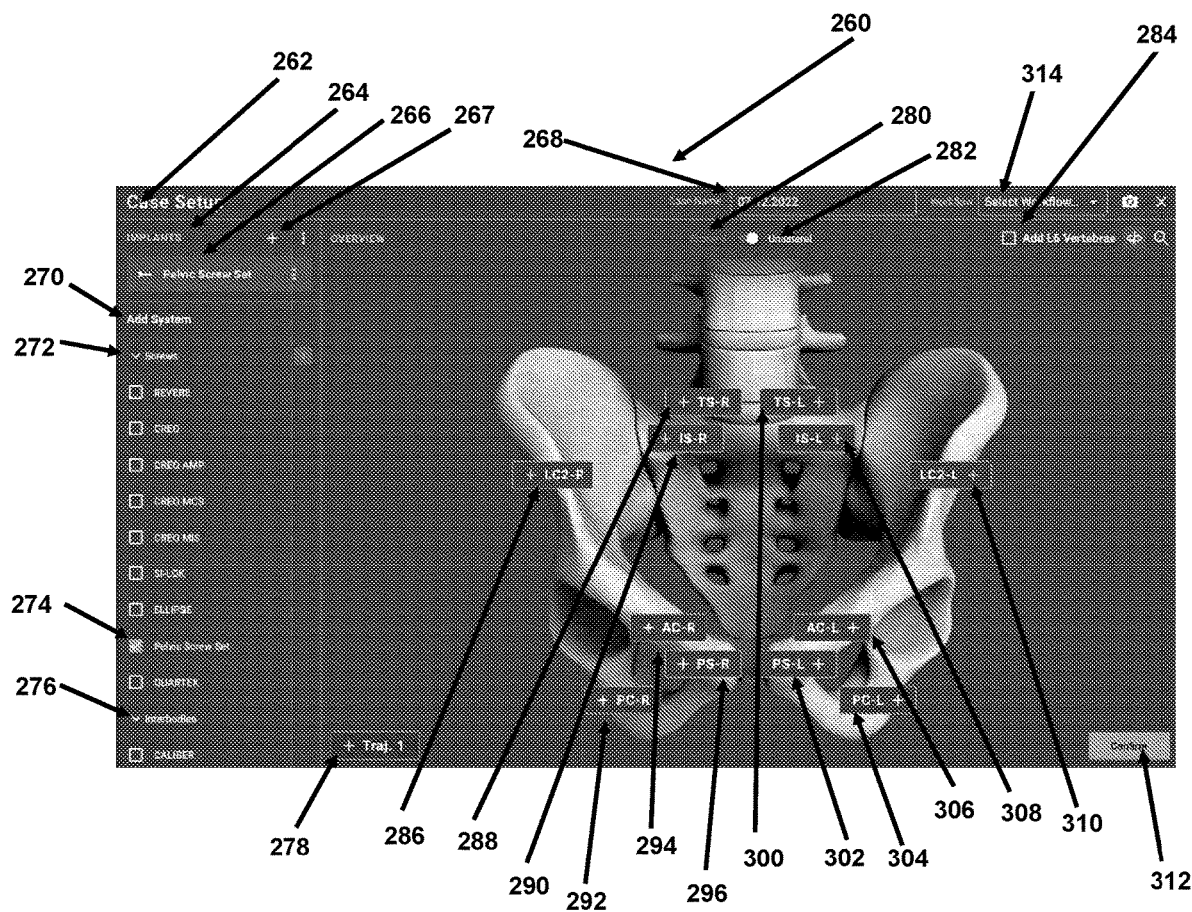
FIG. 5 is a front view of an electronic display screen of implant sets and associated trajectories associated with the present invention.

Once the surgeon selects the proper medical image file 242 or otherwise known as the case file, and is directed to an implant set and trajectories screen that is generally indicated by numeral 260 in FIG. 5, The selected case name is indicated by the numeral 268 on the case setup page 262. The types of implants are listed in the column identified by the numeral 264. In this case, the pelvic screw set is indicated by the numeral 266 under the heading of screws 272 or interbodies 276. There is a click on input 274 to input the pelvic screw set.

If no prior dataset is available, then the surgeon can create a new case file either through input 270 and add additional implants through input 267 or before arriving at the implant set and trajectories screen 260.

The selection of an implant will automatically trigger the surgical robotic system 100 to select the instruments needed for the surgery. This will result in speeding up the instrument selection and verification stage. However, the surgeon will have the ability to add and verify additional instrumentation as needed as well as being able to have the surgical robotic system 100 automatically select screw trajectories such as indicated by numeral 278 as trajectory 1. In addition, the surgical robotic system 100 will recognize the fracture patterns from the patient dataset and group them with a cohort of patients based on the fracture pattern and severity.

These classifications are recited in FIG. 6 and generally indicated by the numeral 320. In addition, there is a column for classifications of injury 322 that includes the type of injury and trajectory selection and three columns for severity 321, which are 324, 326, and 328.

Figure 7:
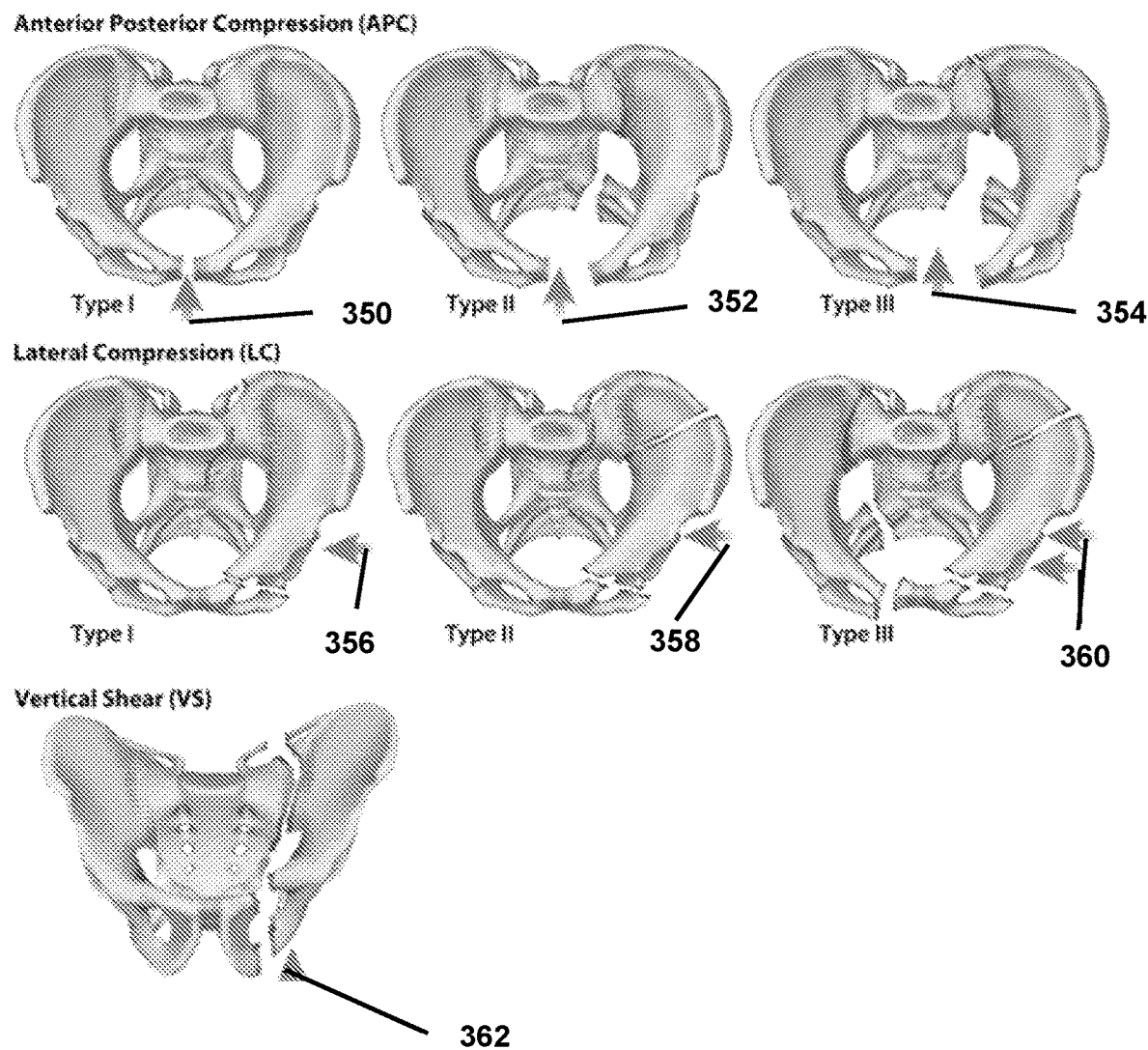
FIG. 7 is a front view of illustrative representations of pelvic fracture classifications from FIG. 6.

The first injury in the first row 330 is anterior-posterior compression (APC) pelvic fracture creates a complete diastasis of the anterior pelvis, which might be associated with bilateral sacroiliac joint injuries and further bilateral arterial injuries, which includes an APC 1 injury, which is a type of pelvic ring injury shown in column 324, which is widely acknowledged as being stable and is shown in FIG. 7 by numeral 350, APC 2 injuries are defined as a disruption of the symphyseal ligaments and the ligaments of the pelvic floor (sacrospinous and sacrotuberous ligaments), shown in column 326. On radiographs, this manifests as a widening of the symphyseal ligaments by more than 2.5 centimeters and as shown in FIG. 7 by numeral 352. Finally, an APC 3 injury is defined as the disruption of the anterior and posterior sacroiliac ligaments, including the posterior sacroiliac complex, the strongest ligaments in the body, in column 328. APC 3 injuries have the highest mortality rate, blood loss, and need for transfusion of all pelvic ring injuries, as shown in FIG. 7 by numeral 354, The anterior-posterior compression (APC) trajectory selection of screws is found in row 332. The first severity is pubic symphysis (PS). The pubic symphysis is a secondary cartilaginous joint located in the midline between the bodies of the pubic bones shown in column 324. The symphysis is composed of the fibrocartilage interpubic disc and surrounding ligaments that comprise a strong fibrous sheet. The second severity is the APC trajectory of screw selections shown in column 326, including iliosacral (IS), which is that relating to the ilium and sacrum, which are bones in the hip and the pelvis, respectively, and transacral (TS) placement aligns the screw horizontally through the sacral ala on both the inlet and outlet views of the sacrum. This is in addition to pubic symphysis (PS). All three of these screw trajectories would be unilateral.

The third severity is the APC trajectory of screw selections shown in column 328, including iliosacral (IS), which is that relating to the ilium and sacrum, which are bones in the hip and the pelvis, respectively, and transacral (TS) placement aligns the screw horizontally through the sacral ala on both the inlet and outlet views of the sacrum. This is in addition to pubic symphysis (PS). All three of these screw trajectories would be unilateral.

The next compression type is Lateral Compression (LC) in row 334. Lateral refers to the sides of something or moving in a sideways direction. There is LC1, a lateral compression fracture in column 324 that refers to crush or "buckle fractures" of the sacrum and is shown in FIG. 7 by numeral 356, LC2 is the fracture line that involves the sacroiliac joint and some of the posteriorly stabilizing ligaments in column 326 and is shown in FIG. 7 by numeral 358, LC3 is also called the 'windswept pelvis' as parts of both iliosacral joints are destroyed in column 356. These fractures may be considered rotationally and vertically unstable and are shown in FIG. 7 by numeral 360. All lateral compression injuries possess typical fracture patterns of the obturator ring.

The screw trajectory for Lateral Compression (LC) is found in row 336. The trajectories for LC1 are found in column 324. This includes the anterior column (AC). The anterior column is defined as the strut of bone that extends from the sacroiliac joint to the ipsilateral pubic ramus. The anterior column includes the superior pubic ramus, anterior half of the acetabulum, anterosuperi- or and anteroinferior iliac spines, and anterior iliac crest. An LC1 screw trajectory also can include the posterior column (PC), which includes the greater and lesser sciatic notches and the ischium and has much less surface area than the anterior column. Finally, the third screw trajectory can include iliosacral (IS), which is that relating to the ilium and sacrum, which are bones in the hip and the pelvis, respectively. All three of these trajectories are unilateral.

The trajectories for LC2 are found in column 326. This includes the anterior column (AC). The anterior column is defined as the strut of bone that extends from the sacroiliac joint to the ipsilateral pubic ramus. The anterior column includes the superior pubic ramus, anterior half of the acetabulum, anterosuperi- or and anteroinferior iliac spines, and anterior iliac crest. An LC2 screw trajectory also can include the posterior column (PC), which includes the greater and lesser sciatic notches and the ischium and has much less surface area than the anterior column. Finally, the third screw trajectory can include iliosacral (IS), which is that relating to the ilium and sacrum, which are bones in the hip and the pelvis, respectively.

The fourth screw trajectory is lateral compression (LC2), which is the fracture line that involves the sacroiliac joint and some of the posteriorly stabilizing ligaments. All four of these trajectories are unilateral.

The trajectories for LC3 are found in column 328. This includes the anterior column (AC). The anterior column is defined as the strut of bone that extends from the sacroiliac joint to the ipsilateral pubic ramus. The anterior column includes the superior pubic ramus, anterior half of the acetabulum, anterosuperi- or and anteroinferior iliac spines, and anterior iliac crest. An LC3 screw trajectory also can include the posterior column (PC), which includes the greater and lesser sciatic notches and the ischium and has much less surface area than the anterior column. Finally, the third screw trajectory can include iliosacral (IS), which is that relating to the ilium and sacrum, which are bones in the hip and the pelvis, respectively.

The fourth screw trajectory is lateral compression (LC2), which is the fracture line that involves the sacroiliac joint and some of the posteriorly stabilizing ligaments. The fifth screw trajectory is transactral (TS), which aligns the screw horizontally through the sacral ala on both the inlet and outlet views of the sacrum. The screw trajectories for the anterior column (AC), posterior column (PC), and iliosacral (IS) are bilateral, while the screw trajectories for lateral compression (LC2) and transactral (TS) are unilateral.

The next compression type is a vertical shear (VC), shown in row 340. A pelvic shear fracture is unstable ipsilateral anterior and posterior fractures of the pelvic ring, with resultant superior displacement of one hemipelvis, and is shown in FIG. 7 by numeral 362.

Under a vertical shear (VS), there is only one column of screw trajectories in row 342 under column 324. This includes the anterior column (AC). The anterior column is defined as the strut of bone that extends from the sacroiliac joint to the ipsilateral pubic ramus. The anterior column includes the superior pubic ramus, anterior half of the acetabulum, anterosuperi- or and anteroinferior iliac spines, and anterior iliac crest. An LC1 screw trajectory also can include the posterior column (PC), which includes the greater and lesser sciatic notches and the ischium and has much less surface area than the anterior column. The third screw trajectory can include iliosacral (IS), which is that relating to the ilium and sacrum, which are bones in the hip and the pelvis, respectively. The fourth screw trajectory is transactral (TS), which aligns the screw horizontally through the sacral ala on both the inlet and outlet views of the sacrum. All four of these screw trajectories are unilateral.

Referring again to the implant set and trajectories screen that is indicated by numeral 260 in FIG. 5, implant selection will automatically trigger the system to select the instruments needed for the surgery. This will speed up the instrument selection and verification stage. However, the surgeon will have the ability to add and verify additional instrumentation as needed and will also be able to have the surgical robot system 100 automatically select screw trajectories. The surgical robot system 100 will recognize the fracture patterns from the patient dataset and group them with a cohort of patients based on the fracture pattern and severity. A particular screw trajectory is indicated in output 278. A right transacral (TS) screw trajectory is shown by the numeral 288, and a left transacral (TS) screw trajectory is indicated by the numeral 300. A right iliosacral (IS) screw trajectory is shown by the numeral 290, and a left iliosacral (IS) screw trajectory is indicated by the numeral 308. A right lateral compression (LC2) screw trajectory is shown by numeral 286, and a left lateral compression (LC2) screw trajectory is indicated by numeral 310. A right anterior column (AC) screw trajectory is shown by the numeral 294, and a left anterior column (AC) screw trajectory is indicated by the numeral 306. A right posterior column (PC) screw trajectory is shown by the numeral 292, and a left pubic symphysis (PC) screw trajectory is indicated by the numeral 304. Finally, a right pubic symphysis (PS) screw trajectory is shown by the numeral 296, and a left anterior column (AC) screw trajectory is indicated by the numeral 302.

There is a click on an input to add L6 vertebrae indicated by the numeral 284. A sixth lumbar vertebra in a spine is uncommon, with about ten percent of the population having this extra bone in this region. While this additional vertebrae does not usually affect health, it can complicate treatment for spinal cord injuries. There is a click on input for bilateral 280 and for unilateral 282 screw attachments. There is a drop-down menu 314 for selecting the workflow. Once the implants and trajectories are selected, then there is a confirmation pushbutton 312.

The next step is to register the instruments and verify that the instruments that are intended to be utilized are the instruments selected. A nonlimiting, but illustrative, example of a system that can perform this function is the aforementioned Globus Excelsius GPS® system.

This preoperative stage will provide a step-by-step user interface for healthcare professionals to plan the reduction and placement of screws and/or plates for the associated disruption of the pelvic ring, acetabulum, or sacrum. This will require imaging of the patient prior to the operation and is then sent to a secure patient database. Then patient data is then processed by the system to analyze and measure the same anatomical landmarks and characteristics as mentioned in the previous section. The system will then group the patient into an associated patient group and determine how much the patient's data varies from the group. If the patient does not have a bilateral injury, the system can also provide data to show how much the affected anatomical landmark varies from the contralateral side. This measured outcome is then sent to the associated patient's file that is in electronic communication with the surgical robotic system 100.

When planning screw trajectories, there are two associated workflows. The first workflow will have the surgical robotic system 100 suggest the ideal trajectory for single or multiple screw placements. These trajectories are derived from the correction needed in view of the patient's anatomy and are automatically planned in the software. These trajectories are also derived from known passageways or "corridors", which avoid veins, arteries, neurovascular bundles, gastrointestinal, and reproductive systems and do not breach or exit boney anatomy. These automatically planned trajectories will be able to be edited by the user if they feel they need to adjust or want to achieve a different desired outcome from what the surgical robotic system 100 suggests. The second workflow will have the surgeon plan the screw trajectories manually. The surgical robotic system 100 will alert the surgeon if they are planning a trajectory that does not correlate with the acceptable level of error/criteria. For example, suppose the user decides to deviate from the suggested trajectories. In that case, the surgical robotic system 100 will keep track of these changes through machine learning and continuously adjust the suggested trajectories based on the amount of correction from the surgeon.

The next step in the process is for the surgeon to perform any reduction methods necessary to reduce the fracture to natural alignment. This includes pelvic clamps, binders, Shanz pins, plates, and screws. When planning or measuring fracture reduction, the surgeon will then assign or identify anatomical landmarks or bone fragments they wish to correct/measure. The surgical robot system 100 will inform the user how much the patient's anatomy varies from either the patient's uninjured natural anatomy or from the anatomical database.

Figure 8:
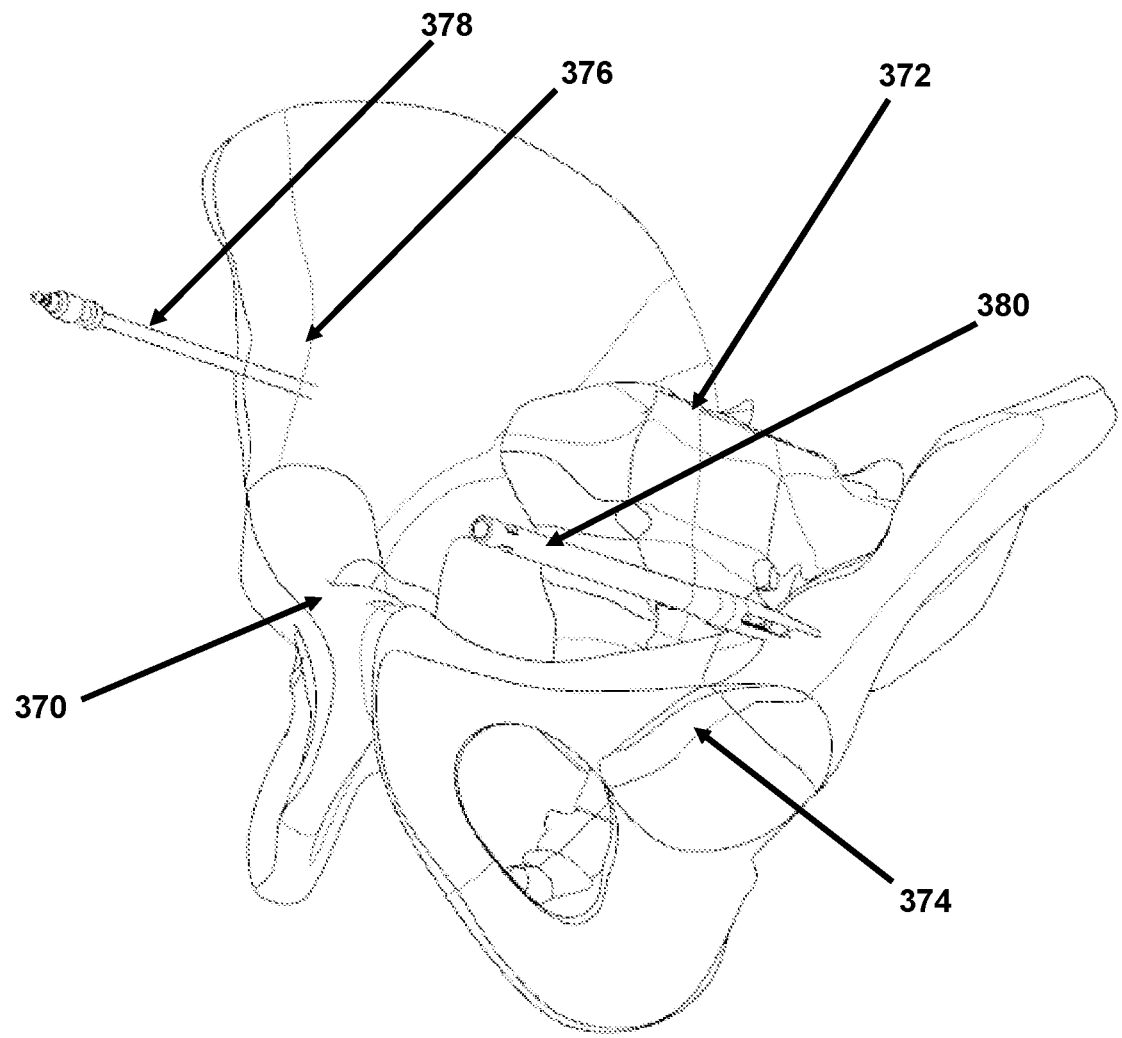
FIG. 8 is a perspective view of a patient's pelvic area utilizing a surveillance marker and bone anchor spike to determine patient positioning for CT imaging.

Once the surgeon has completed all other steps, they can then proceed to register the patient's anatomy. Referring now to FIG. 8, a patient's pelvis 370, sacrum 372, acetabulum 374, and the anterior superior iliac spine (ASIS) 376 are shown. The surgeon will first place a surveillance marker (SM) 378 on one side of the patient's anterior superior iliac spine (ASIS) 376. The surveillance marker (SM) 378 is a single reflective marker used to monitor a patient's physical shift. Surveillance markers may be used alone or in conjunction with a bone clamp. The use of a surveillance marker further confirms the accuracy of the images in relation to real-time patient anatomy. In addition, the surveillance marker (SM) 378 can provide an alert when there is patient movement and, if necessary, re-register the patient. Surveillance markers (SM) 378 are directly inserted into the iliac crest or long bone or may be attached to the spinous process using a bone clamp. A bone anchor spike 380 is then placed contralaterally on the anterior superior iliac spine (ASIS) 376, from where the surveillance marker (SM) 378 is placed. An illustrative, but nonlimiting, example of a bone anchor is a Quattro™ spike, which is a trademark of Globus Medical Inc., having a place of business at 2560 General Armistead Ave, Audubon Pennsylvania 19403. Preferably, the bone anchor spike 380, when driven with a mallet into the bone, such as the iliac crest, engages at least three spikes and preferably four small spikes to provide anchoring that prevents bending and rotation. A single post is susceptible to a rotation about its central shaft and bending in any direction, and a pair of posts prevent the rotational risk of a single post. Still, there may be susceptibility to bending perpendicular to the line formed between the posts.

Figure 9:
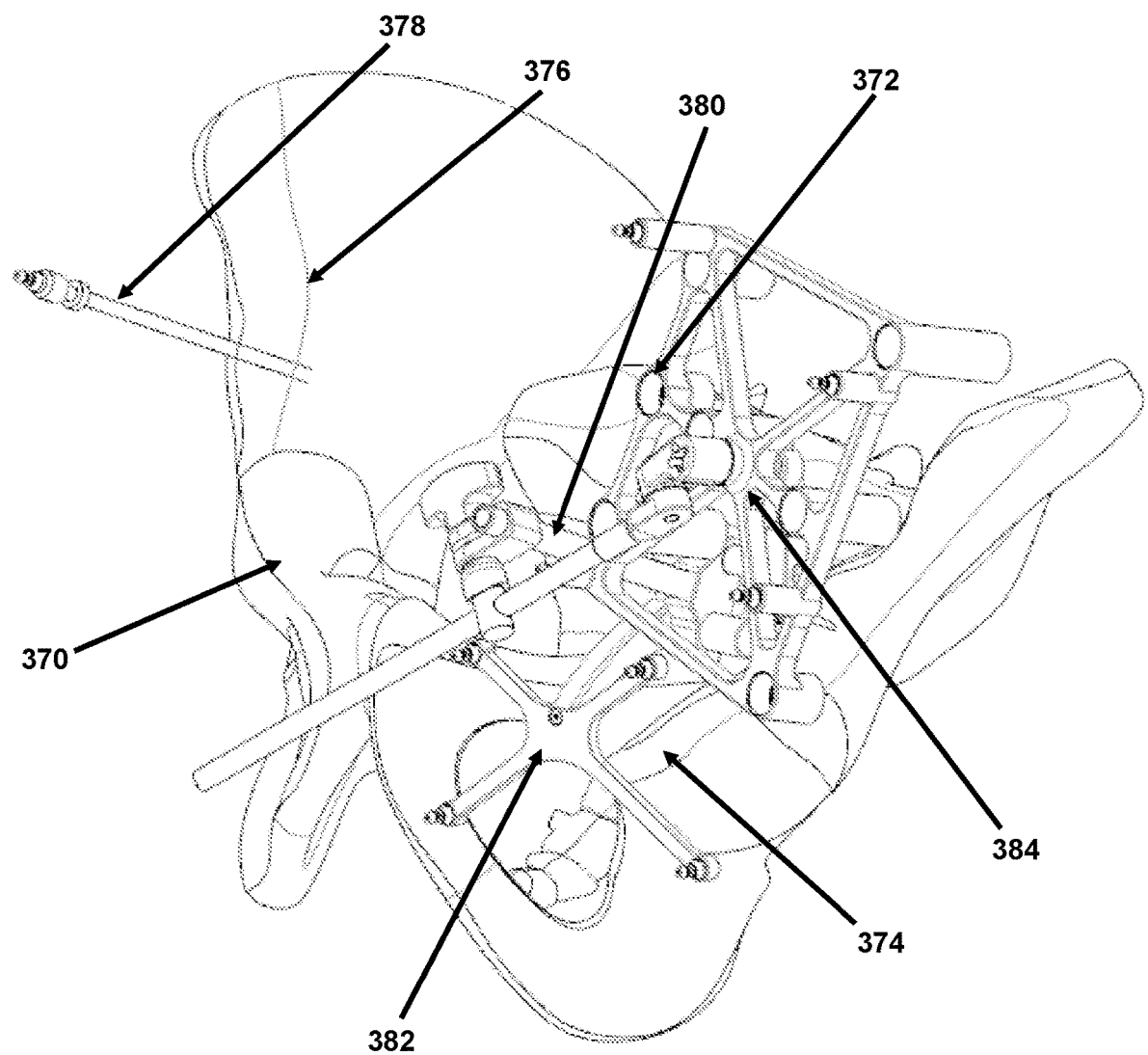
FIG. 9 is a perspective view of a patient's pelvic area utilizing a dynamic reference base array, interoperative CT registration fixture, and surveillance marker to determine patient positioning for CT imaging.

Referring now to FIG. 9, for a computed tomography (CT) platform other than one manufactured by Globus Medical Inc, a dynamic reference base array (DRB) 382 and the surveillance marker 378 are then affixed to the sacrum 370. The surgeon assembles the dynamic reference base array (DRB) 382, the CT registration fixture (ICT) 384, to the bone anchor spike 380. These markers are positioned with a superolateral trajectory. This intraoperative CT registration fixture 384 is operatively positioned with respect to the dynamic reference base array 382. An intraoperative computed tomography (CT) from various manufacturers can be performed and is coregistered to the patient's preoperative imaging. A trajectory plan may then be created for each implant, e.g., navigated screw. Alternatively, screw trajectories may be preplanned before the procedure using a preoperative computed tomography (CT) scan to decrease intraoperative time. Trajectory screw plans may be adjusted and confirmed at this point in time. The end effector 112, referring again to FIGS. 1 and 2, then moves into position to guide all movements along this planned trajectory and all subsequent steps. A fluoro fixture should also be utilized with some types of surgical robotic systems not manufactured by Globus Medical Inc.

Figure 10:
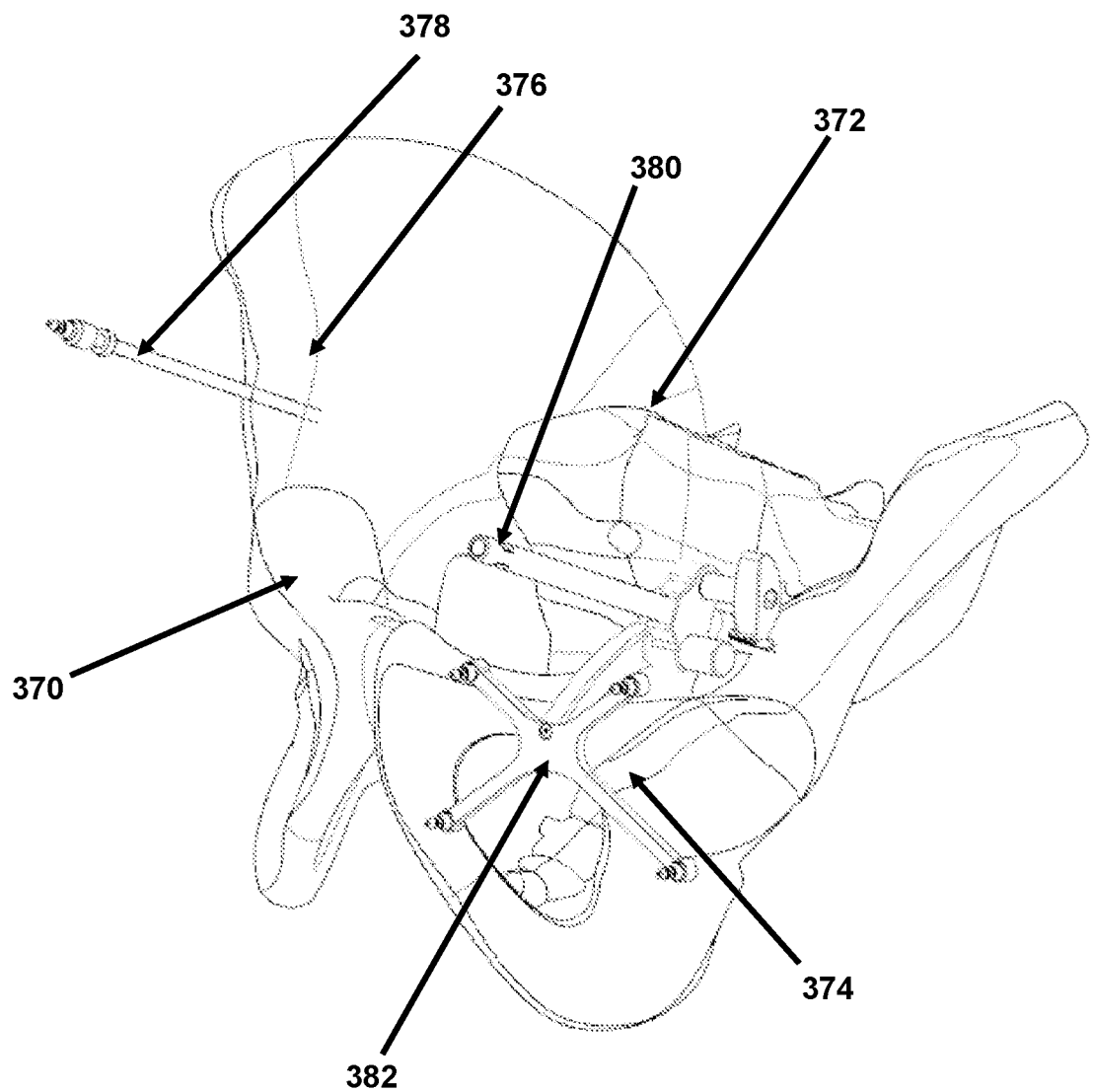
FIG. 10 is a perspective view of a patient's pelvic area utilizing a dynamic reference base array, surveillance marker, and bone anchor spike to determine patient positioning for CT imaging.

Referring now to FIG. 10, in some types of surgical robotic systems 100, e.g., EXCELSIUS3D™, the surgeon only needs to assemble the dynamic reference base array (DRB) 382 to the bone anchor spike 380, e.g., Quattro™ spike. Therefore, this application does not need a CT registration fixture (ICT).

The surgeon and hospital staff will then take a CT scan of the patient and registration fixtures. The surgeon will then capture all images needed and push the collected data to the case file. The surgeon will then ensure all surveillance markers are visible and perform anatomical landmark checks to verify CT data matches the current position and alignment of the patient's anatomy.

Figure 11:
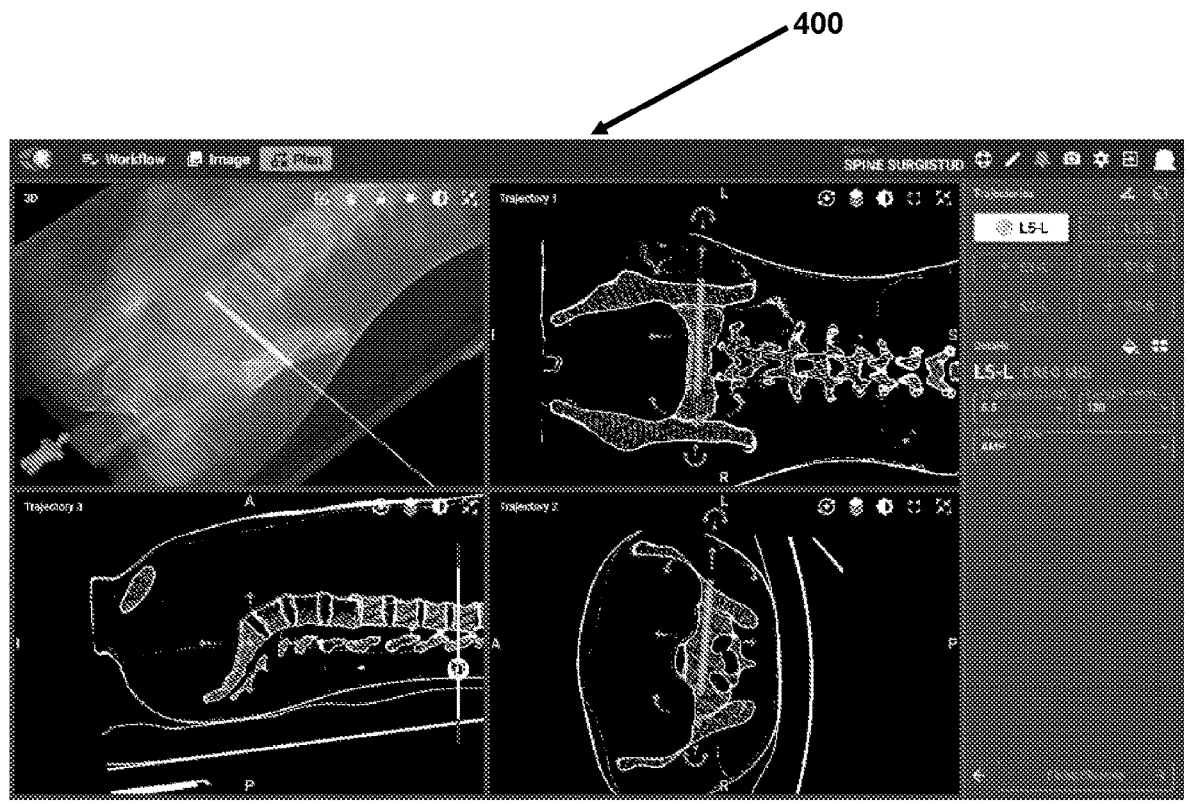
FIG. 11 is a front view of an electronic display of a planning screen, including a 3D CT Scan and 2D cross-sectional views.

Referring now to FIG. 11, the planning screen is generally indicated by the numeral 400. On this electronic display screen 400, the surgeon will be able to view the 3D CT Scan and 2D cross-sectional views. If the surgeon is planning manually, the surgeon will drag and drop the implant selection onto the corresponding trajectory. Once placed, the surgeon will have the option of fine-tuning the implant to suit the patient best, as well as the patient's anatomy.

Figure 12:
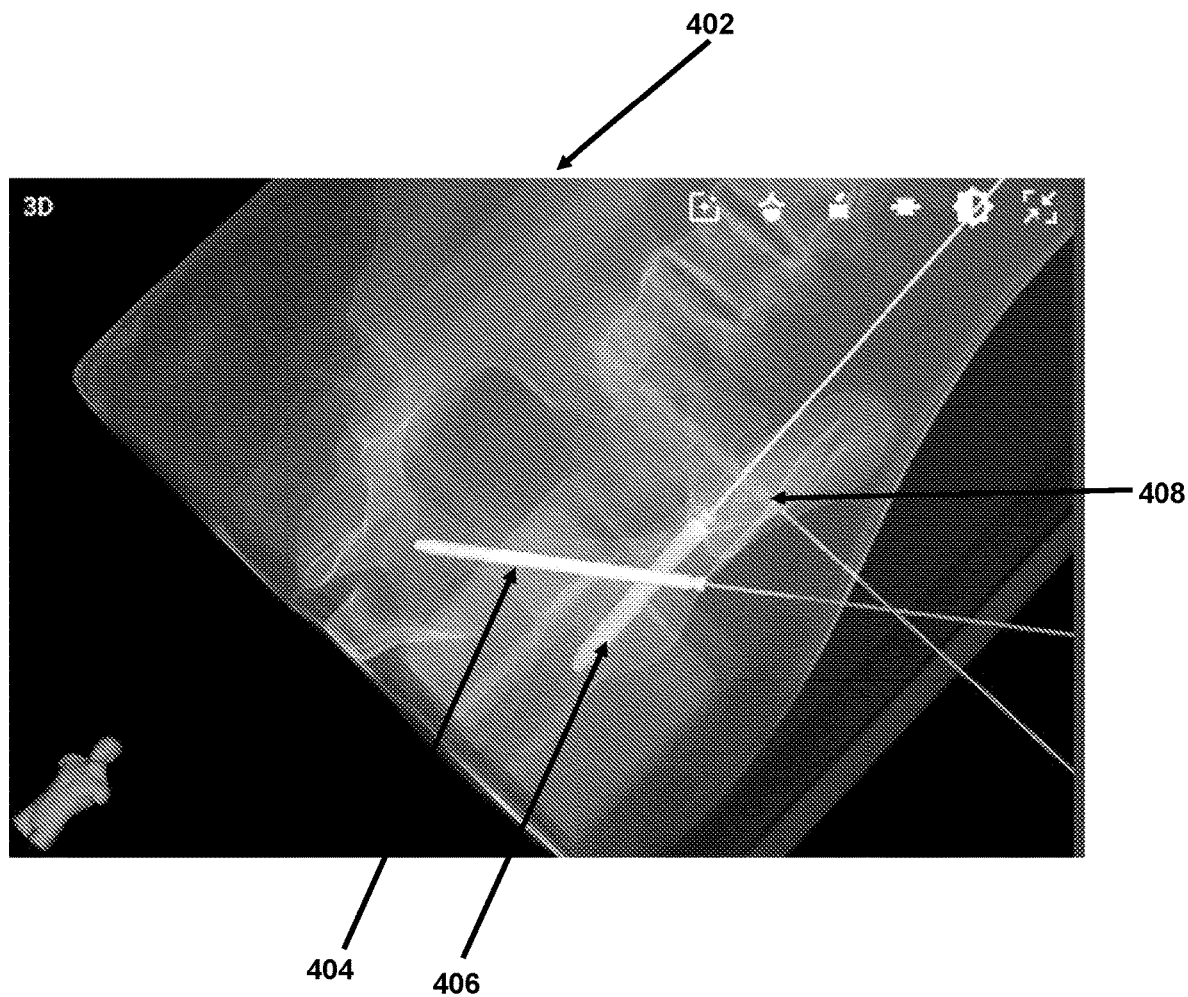
FIG. 12 is a front view of an electronic display of a planning screen showing implants and associated trajectories.

Referring now to FIG. 12, the surgeon will repeat this process until all required implants/trajectories are planned as generally indicated by the numeral 402 with the implants and associated trajectories indicated by numerals 404, 406, and 408, respectively, shown on an electronic display screen. Once all of the necessary implants are planned, the surgeon will then move to navigation.

Once the desired screw trajectory is achieved, the surgeon will select the implants the surgeon would like to use. There will also be two associated workflows: an automated/suggested implant selection and placement and a manual workflow where the surgeon will manually select the implants needed and manually define the location and orientation to achieve the desired outcome. With the automated workflow, the surgical robotic system 100 will correlate the planned trajectories, patient anatomy, and desired outcomes to automatically select the implant's optimal size, location, and orientation. The surgeon will be able to adjust the suggested surgical implants manually as needed. As with the automated screw trajectories, the surgical robotic system 100 will continuously learn how much the surgeon adjusts from the suggested size, location, and orientation. The manual workflow will allow the surgeon to manually plan the implants' size, placement, and orientation. These implants will include but are not limited to screws and plates.

Figure 13:
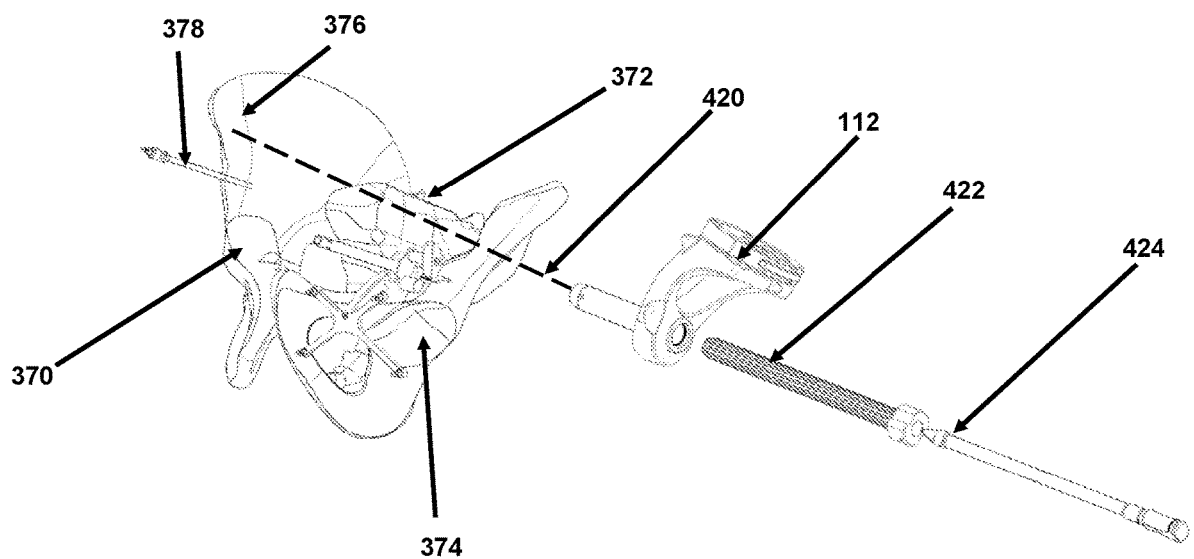
FIG. 13 is a perspective view of equipment for performing skin incisions and dilating a patient's soft tissue, including an end effector that guides a trocar that passes through a soft tissue sleeve along a planned trajectory.

After the desired implant is positioned, machine learning will track what the surgeon has planned. A visual indication will relay information to the user on whether the implant's size, placement, and orientation have achieved the desired outcome. If the surgeon is satisfied, this data is then saved to a secured location to be retrieved once it is time for the surgical procedure The next step in the workflow process is navigation, followed by implant placement. Referring now to FIG. 13, the surgeon will then select the desired and planned trajectory 420 in the patient's pelvis. 370. Next, the surgeon will navigate the surgical robot system 100 as necessary. The surgeon will then perform a skin incision and dilate the patient's soft tissue as necessary. Next, the end effector 112 will guide a trocar 424 that passes through a soft tissue sleeve 422 along the planned trajectory 420. During minimally invasive surgeries, trocars make small, puncture-like incisions in outer tissue layers. These incisions allow surgeons to introduce other surgical instruments. In addition, the soft tissue sleeve 422 allows protection of the surrounding soft tissue during surgery.

Figure 14:
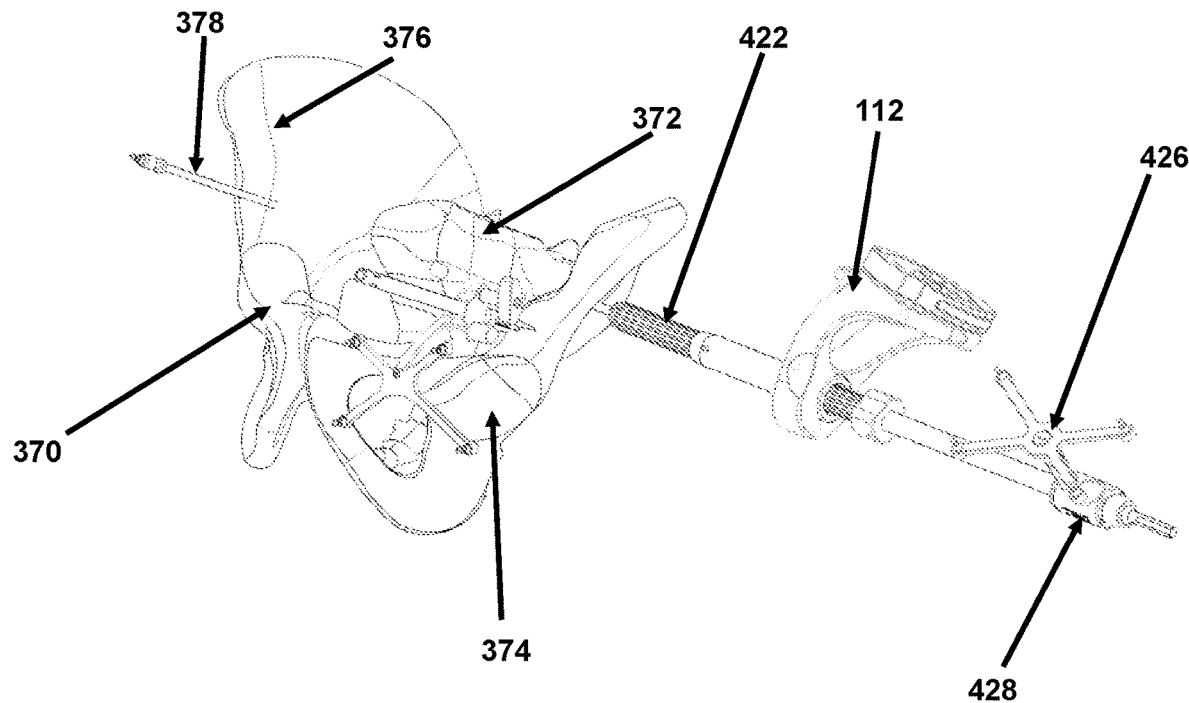
FIG. 14 is a perspective view of equipment for drilling or tapping, e.g., drill array, held by a robotic end effector of implants, e.g., screws, along a planned trajectory.
Figure 15:
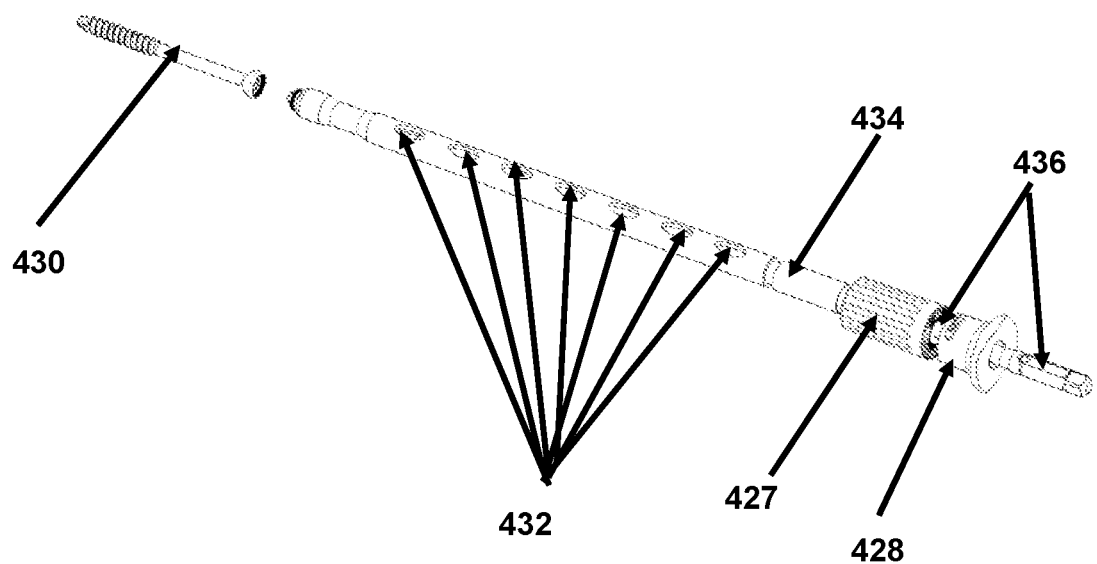
FIG. 15 is a perspective view of a navigated screw loaded into a navigated driver with a series of holes and a spindle that rotates by way of the navigated driver, which in turn rotates the navigated screw.

A navigated drill/tap assembly 426 is shown in FIG. 14, which includes a drill 428 for performing a drilling and taping function and an associated drill cover 427, shown in FIG. 15. The surgeon will then load a navigated screw 430 into a navigated driver 434. There are a series of holes 432 along the length of the navigated driver 434. In addition, there is a spindle 436 that rotates due to the navigated driver 434, that in turn rotates the navigated screw 430.

Figure 16:
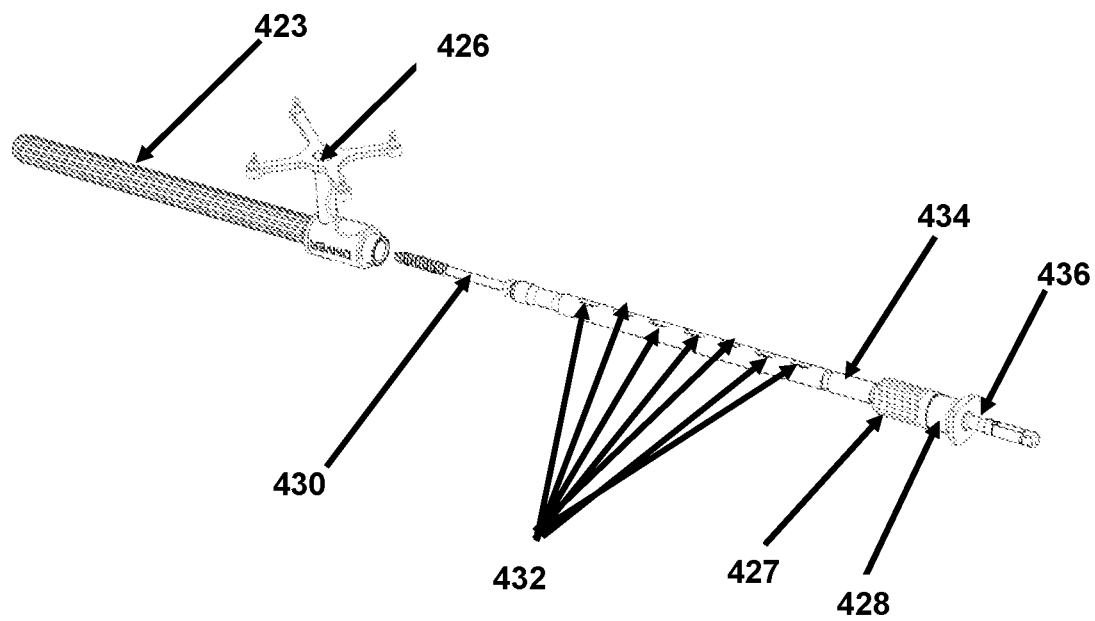
FIG. 16 is a perspective view of the navigated driver array/soft tissue sleeve assembly that can be slid over the screw/driver assembly of FIG. 15.
Figure 17:
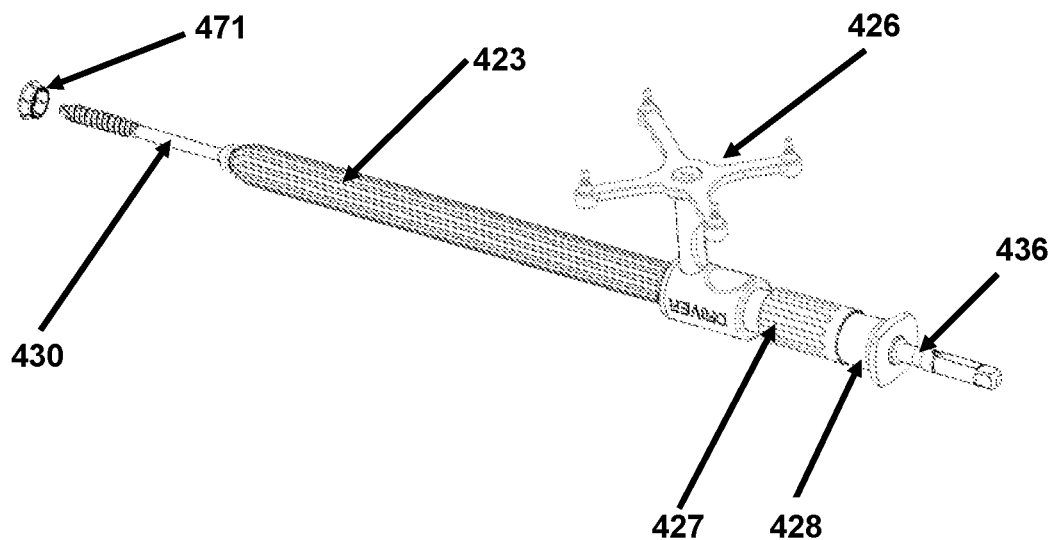
FIG. 17 is a perspective view of a captured washer that can be slid onto the navigated driver array/soft tissue sleeve assembly of FIG. 16.
Figure 18:
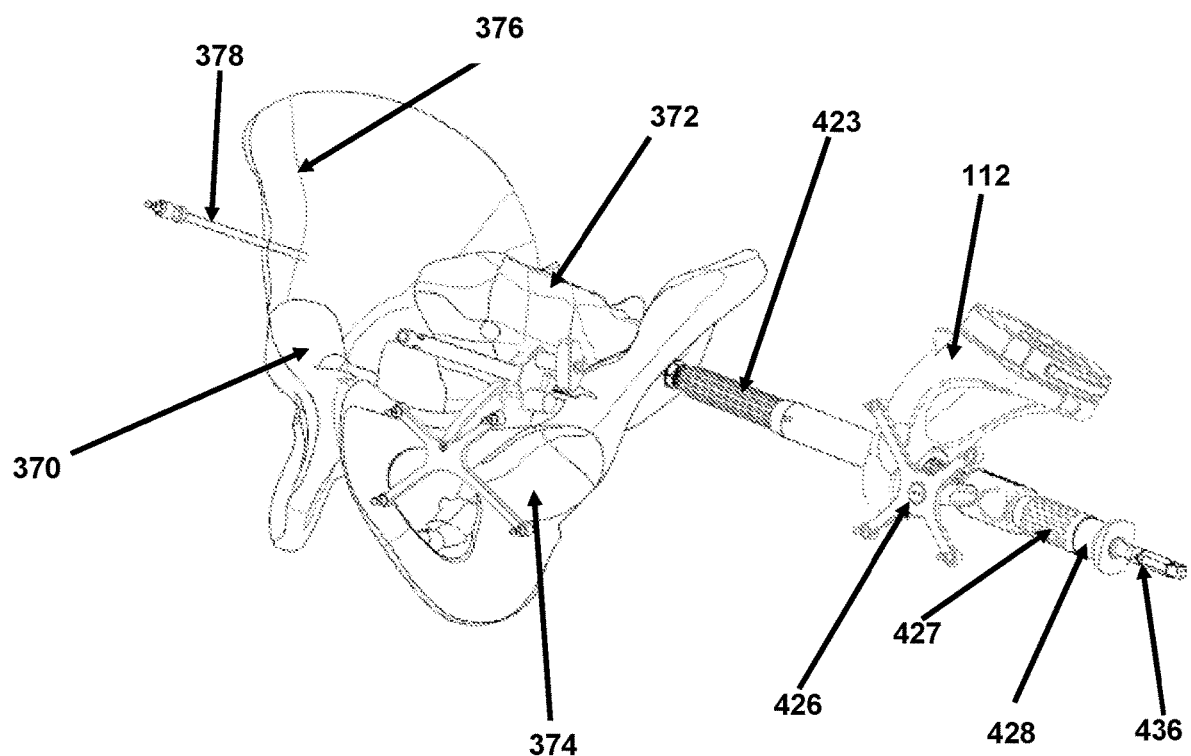
FIG. 18 is a perspective view of a navigated washer/screw/driver assembly from FIG. 17 inserted through the end effector at a desired trajectory and for placing an implant at a desired trajectory and depth.

Referring now to FIG. 16, the navigated driver array 426 and a navigated driver sleeve 423 can be slid over the navigated screw 430 into a navigated driver 434. Referring now to FIG. 17, which shows the navigated driver array 426 and navigated driver sleeve 423 completely slid over the navigated screw 430 into a navigated driver 434 shown in FIG. 15. There is also a captured washer 471 that is attached to the end of the navigated screw 430. The surgeon can then insert the navigated driver array 426 through the end effector 112 at the desired trajectory and implant at the desired depth, as shown in FIG. 18.

Figure 19:
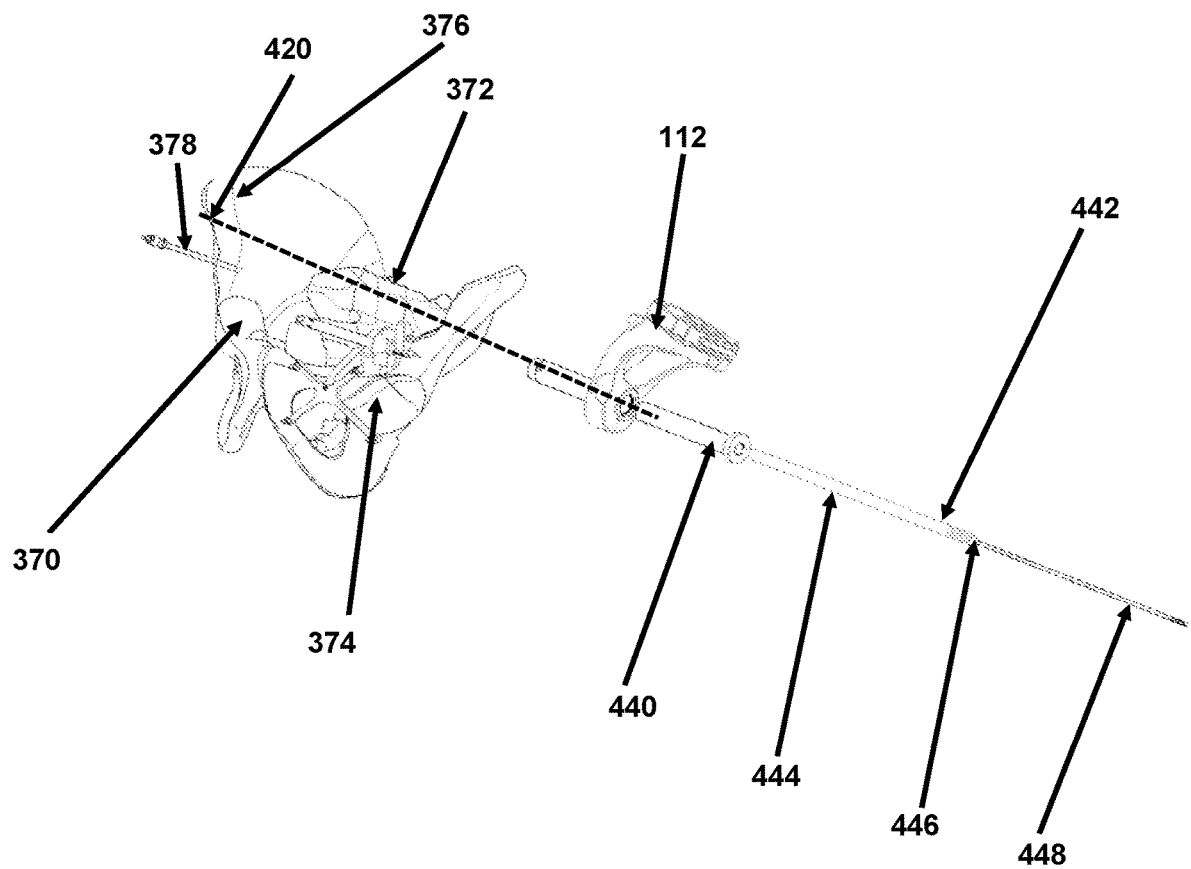
FIG. 19 is a perspective view of an application utilizing a navigated screw with a robotic end effector, a guide sleeve, and a cannula with a k-wire.

Referring to FIG. 19, should the surgeon need or want to place a screw 430 (for example, a screw from a different vendor that cannot be navigated) using a k-wire 448, the surgeon would then need to switch to utilizing the following procedure after the implant selection and planning phase. First, the surgeon will dilate the soft tissue in the patient's pelvis 370, sacrum 372 acetabulum 374 or anterior superior iliac spine (ASIS) 376 as needed using the end effector 112, a guide sleeve 440, a cannula generally indicated by numeral 442 with both a cannula A 444 and cannula B 446 with the k-wire 448.

K-wires, which are also known as Kirschner wires or pins, are sterilized, sharpened, smooth stainless-steel pins. They come in different sizes and hold bone fragments together, i.e., pin fixation, or provide an anchor for skeletal traction. The pins are often driven into the bone through the skin. For example, the k-wire 448 drives the screw 430 via the cannula 442 to a precise location. For this present invention, a wide variety of pins, guides, and so forth can be used instead of k-wire.

Figure 20:
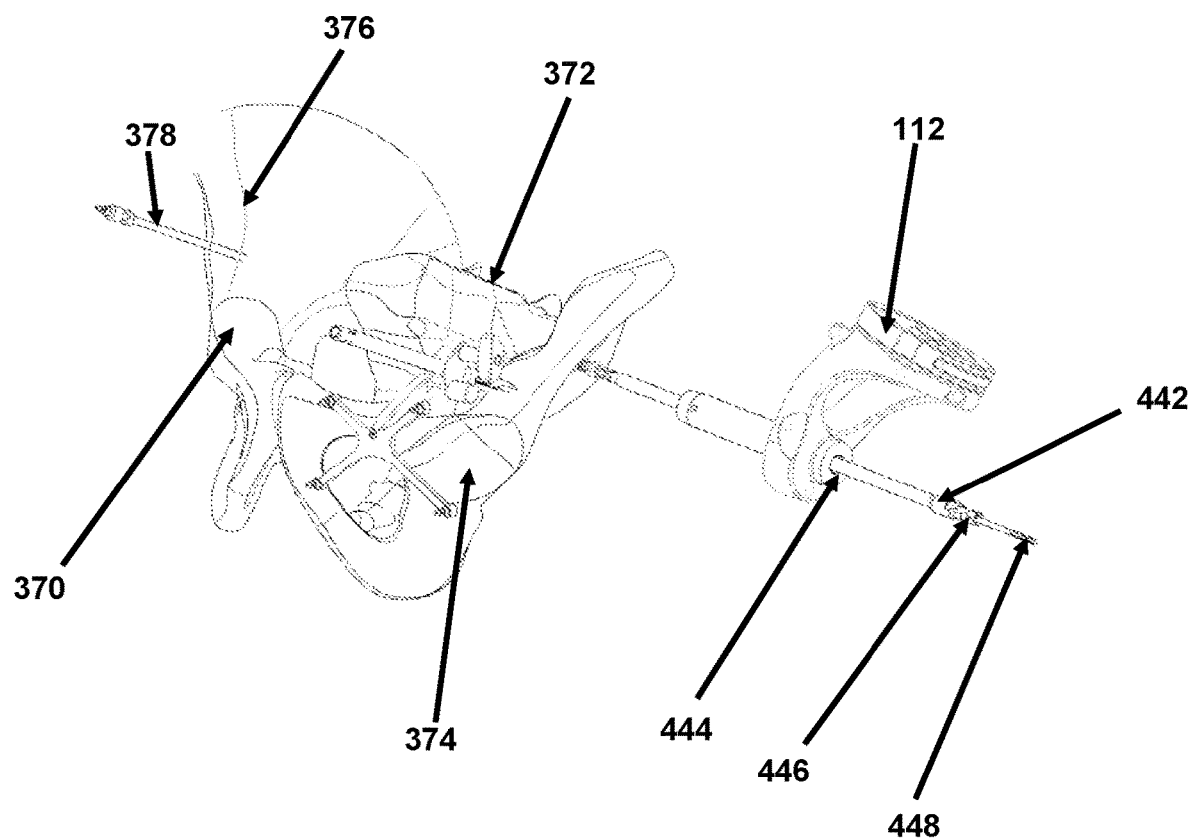
FIG. 20 is a perspective view of a non-navigated screw and driver utilizing the k-wire of FIG. 19 through the guide sleeve until the screw has reached a desired location0.

The surgeon can then remove the cannula 442 and insert the desired drill/tap over the k-wire 448 through the guide sleeve 440 until the desired depth is achieved. Next, the surgeon will insert the required non-navigated screw 430 which is attached to a driver assembly 426 over the k-wire 448 and through the guide sleeve 440 until the non-navigated screw 430 has reached the desired location, as shown in FIG. 20.

The surgeon will repeat this process until all non-navigated screws 430 are adequately placed. The surgeon will then suture all incisions and proceed to finish the operation.

Figure 21:
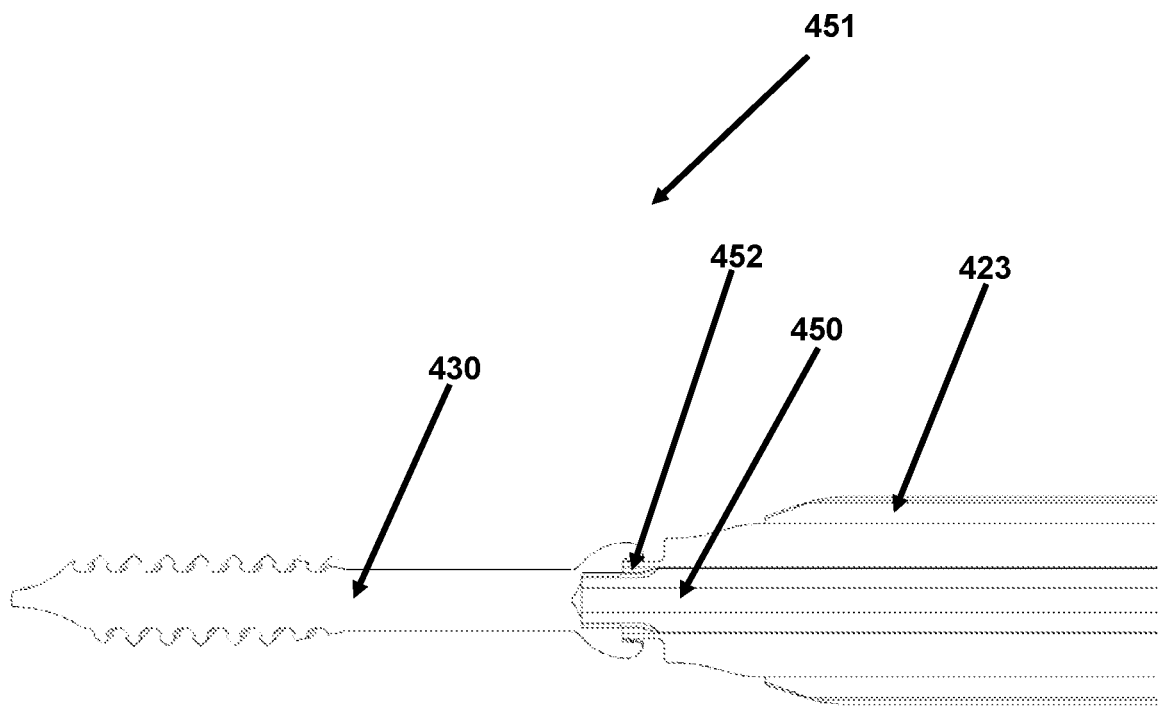
FIG. 21 is a side view of a navigated screw associated with the present invention, including a hexalobular driver positioned within a driver sleeve where the hexalobular driver is inserted within a navigated screw and includes a threaded portion that provides a locking interconnection between the navigated screw and the hexalobular driver.

There are numerous ways of securing the navigated screw 430. The first way is a threaded driver internal interconnection shown in FIG. 21 and generally indicated by the numeral 451, which includes a hexalobular driver 450 positioned within the aforementioned driver sleeve 423. The hexalobular driver 450 is inserted within the navigated screw 450 and includes a threaded portion 452 that provides a locking interconnection between the navigated screw 430 and hexalobular driver 450.

Figure 22:
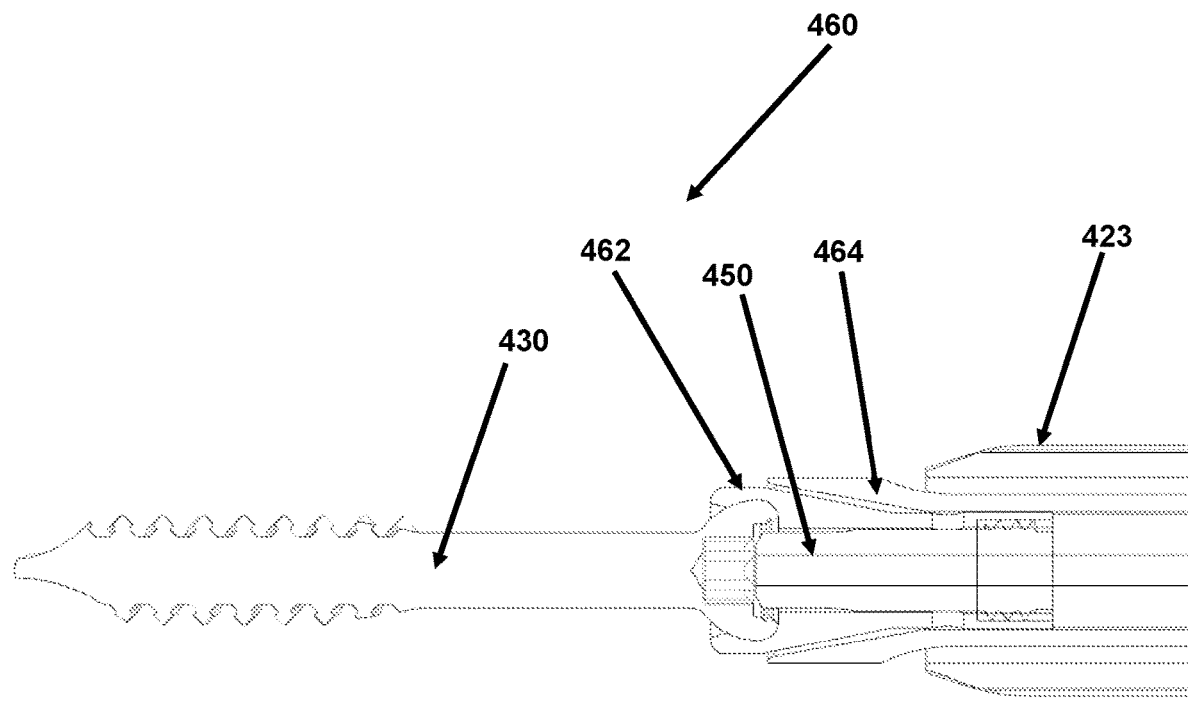
FIG. 22 is a side view of a collet driver interconnection that includes a hexalobular driver positioned underneath a collet that is held into position by a collet sleeve where the hexalobular driver is inserted within the navigated screw under the external pressure of the collet.

A second way is a collet driver interconnection shown in FIG. 22 and indicated by numeral 460, which includes a hexalobular driver 450 positioned underneath a collet 462 that is held into position by a collet sleeve 464 within the aforementioned driver sleeve 423. The hexalobular driver 450 is inserted within the navigated screw 430 utilizing the external pressure of the collet 462 to provide a strong interconnection between the navigated screw 430 and the hexalobular driver 450.

The navigated hexalobular driver 450 can then provide real-time tracking of the tip of the navigated screw 430 to provide feedback to the surgeon on the alignment and accuracy of the placement of the navigated screw 450 compared to the planned trajectory. The surgeon will then place the navigated screw 430 and repeat the remaining trajectories/fractures as needed.

Figure 23:
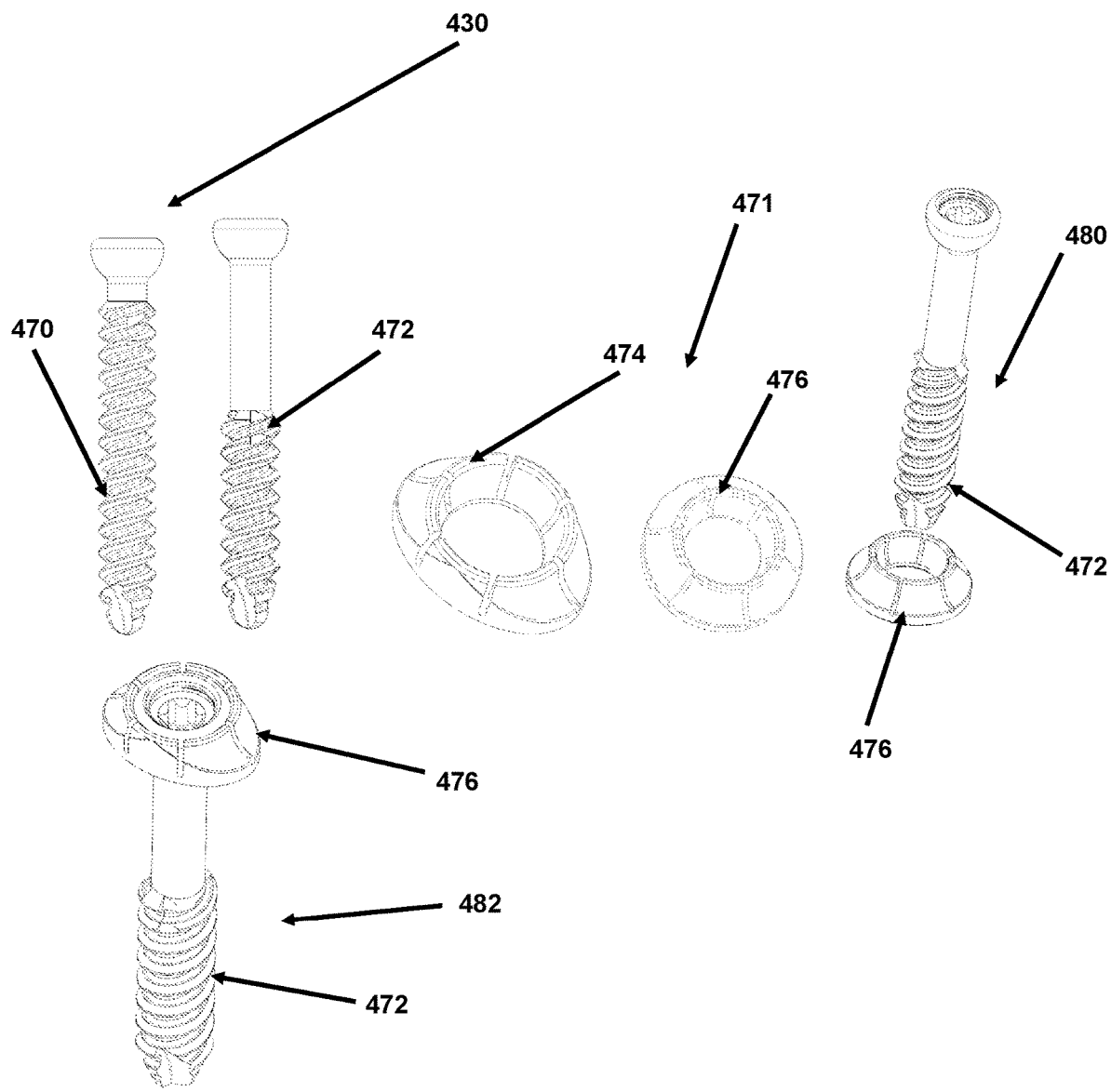
FIG. 23 are perspective views of fully threaded and partially threaded navigated screws and oval and round captured washers in assembled and unassembled states.

Referring now to FIG. 23, the navigated screw 430 can be in the form of a fully threaded hexagonal navigated screw 470 or a partially threaded hexagonal navigated screw 472. In addition, the previously referenced captured washer 471 from FIG. 17 can be in the form of a captured oval washer 474 or a captured round washer 476. Therefore, the unassembled combination of the partially threaded hexagonal navigated screw 472 and the captured round washer 476 is shown by the numeral 480, and the assembled combination of the partially threaded hexagonal navigated screw 472 and the captured round washer 476 is shown by the numeral 482.

Figure 24:
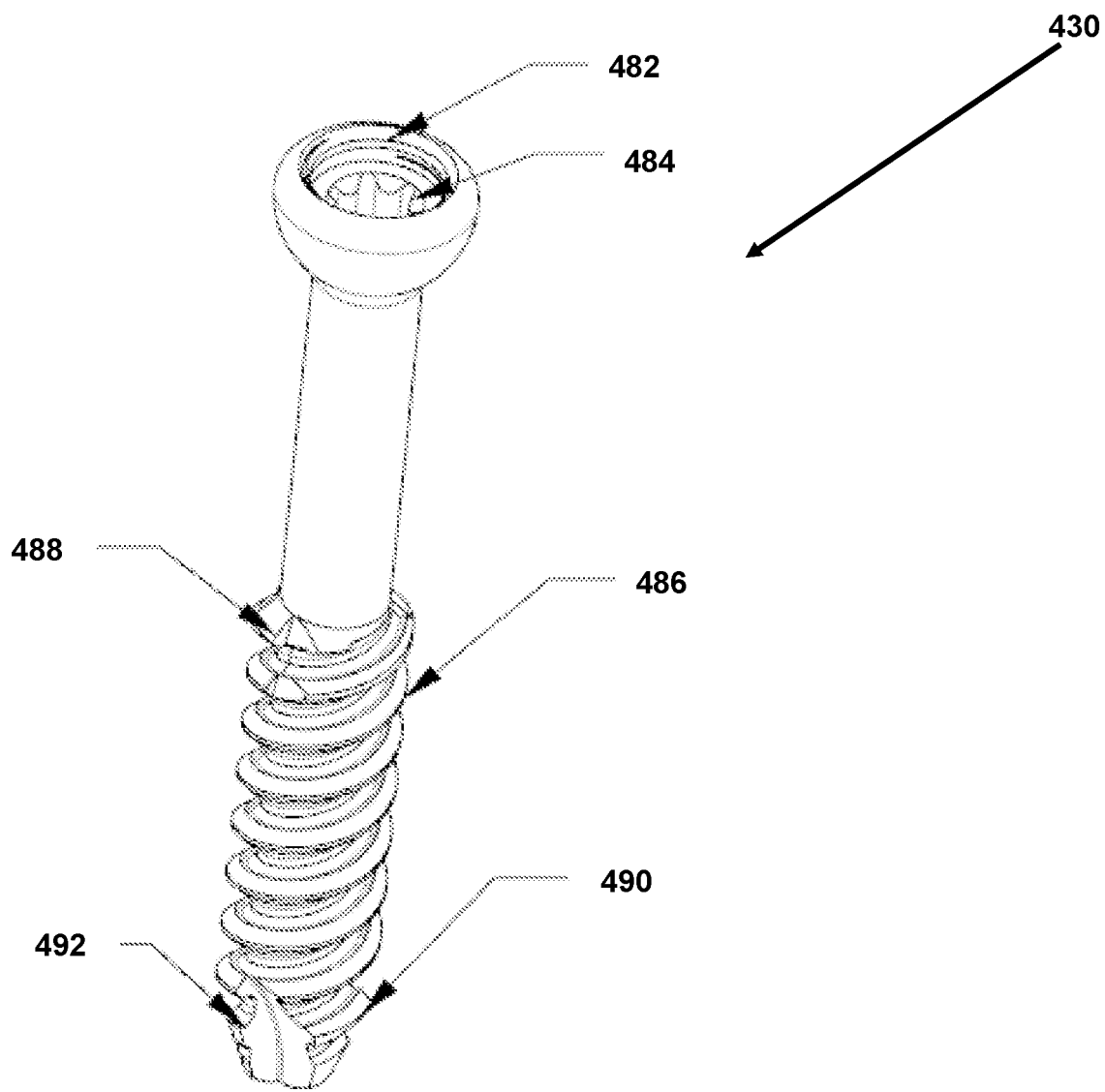
FIG. 24 is a perspective view of a navigated screw of the present invention with additional details regarding threading, hexalobular drive, driver connection, and flutes.

Further details of the navigated screw 430 are shown in FIG. 24. The includes bone interlock thread geometry with an optional solid core 486 to promote bone retention and prevent implant toggle. The navigated screw 430 has the optional solid core that is currently being utilized and increases the shear strength of the navigated screw 430. The navigated screw 430 will include a hexalobular drive 484. This drive size will vary depending on the implant diameter. The navigated screw 430 will have a captured drive connection 482, allowing the implant to mate to either navigated instrumentation or can be utilized in a non-navigated context. The navigated screw 430 will have a tapered tip 490 that will allow the screw to find or pilot into the previously drilled hole. To ease insertion, the navigated screw 430 will also have cutting flutes 492 at the distal tip of the navigated screw 430. The navigated screw 430 will have reverse cutting flutes 488 at the proximal end where the thread terminates to the body of the navigated screw 430, and these reverse cutting flutes 488 will allow the navigated screw 430 to be removed after implantation.

Figure 25:
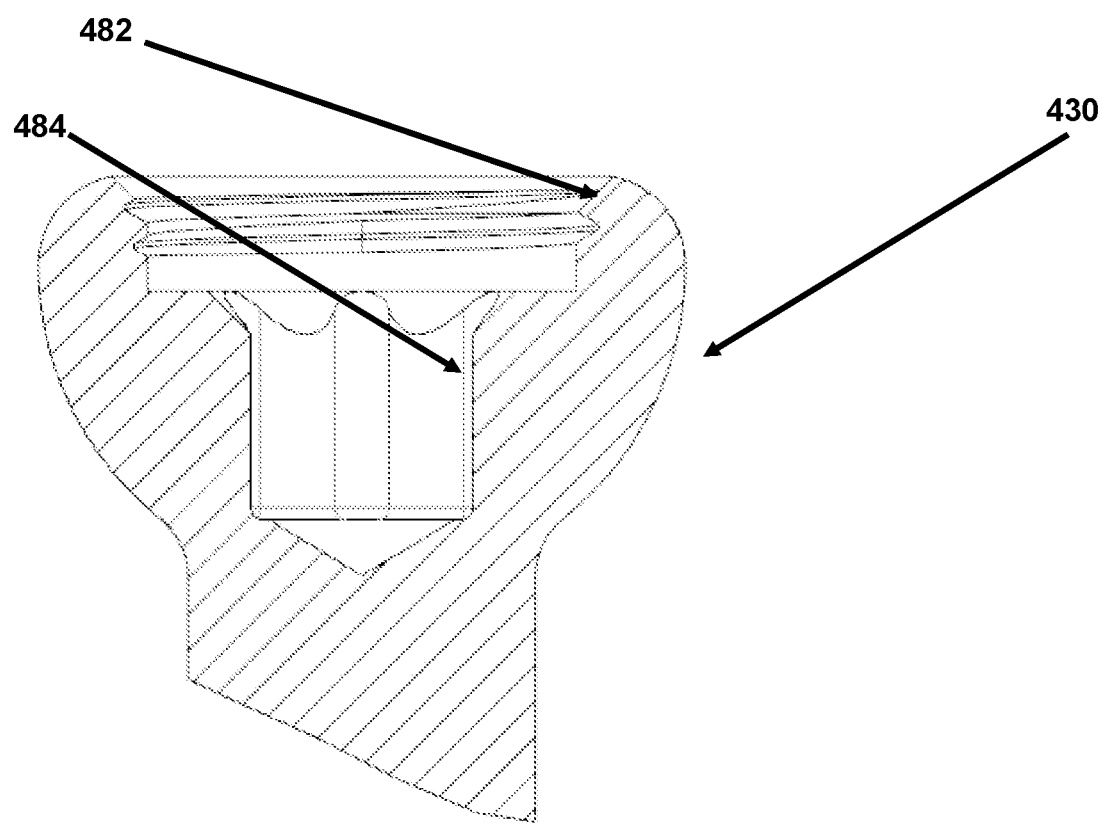
FIG. 25 is an isolated view of an upper portion of a navigated screw with a left-handed thread connection and hexalobular drive.
Figure 26:
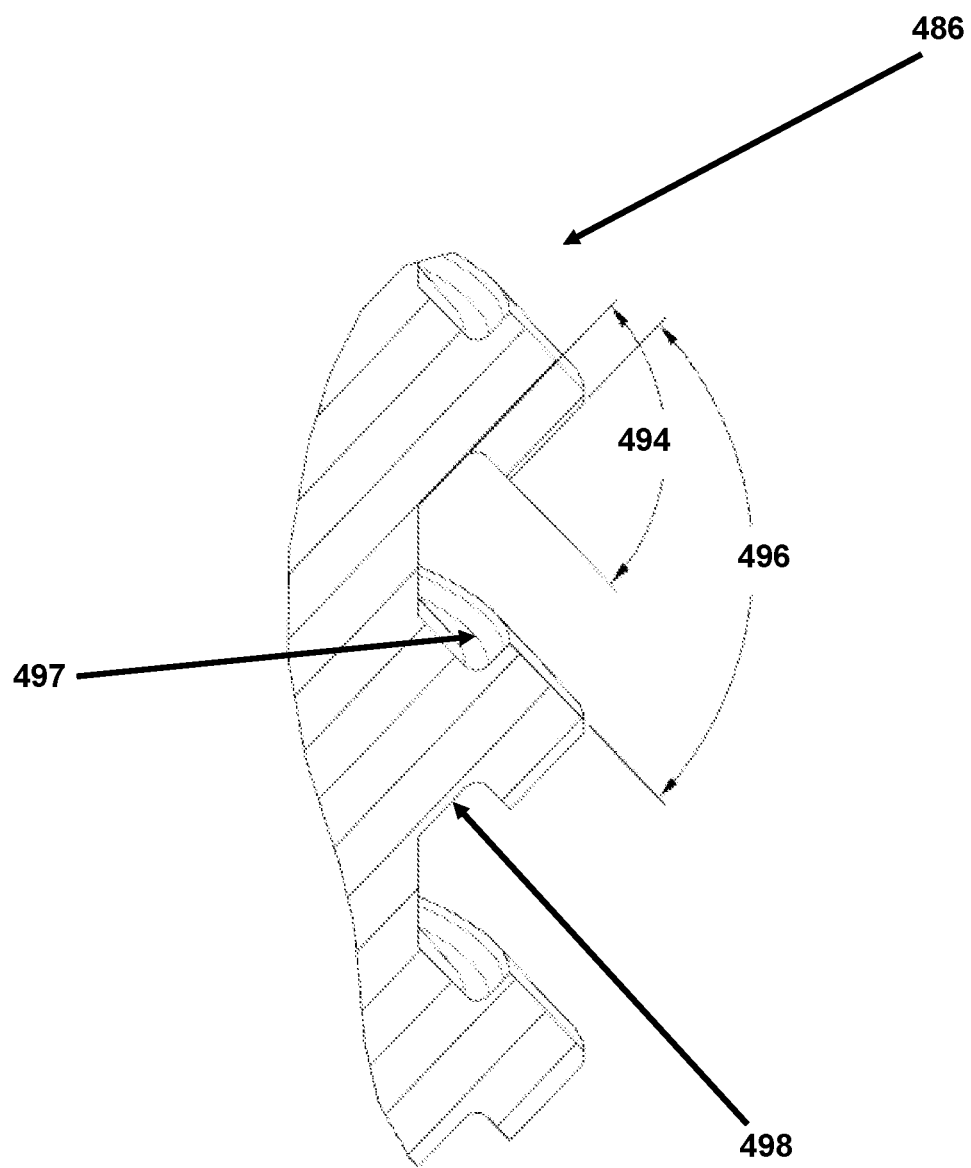
FIG. 26 is an isolated view of a middle portion of a navigated screw with bone interlock thread geometry with both first and second angles and with threads having a top undercut and a bottom undercut.

Referring to FIG. 25, the captured driver connection 482 and the hexalobular drive 484 for the navigated screw 430 are shown in additional detail. The bone interlock thread geometry 486 is shown in greater detail in FIG. 26. This includes a first angle 494 and a second angle 496. These angles 494 and 496 can vary significantly depending on the various anatomical needs of the human pelvis, with ninety-degree angles as an illustrative, but nonlimiting, example for both angles. In addition, the bone interlock thread geometry 486 has a top undercut 497, and a bottom undercut 498 that varies from commercially available navigated screws having only a top undercut.

Figure 27:
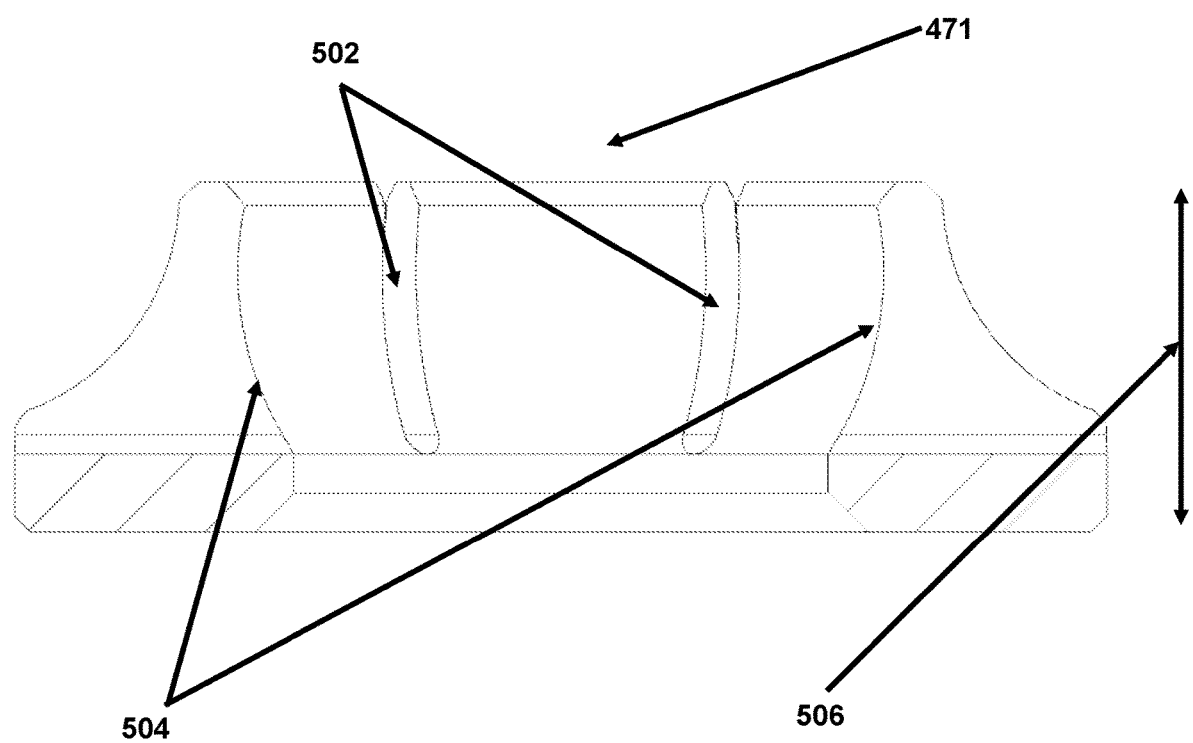
FIG. 27 is a side view of a captured washer associated with the present invention having an internal spherical radius that is designed to contour to the head of a navigated screw and flexural grooves designed to flex and spring back to secure the navigated screw.

As shown in FIGS. 23 and 27, the captured washer 471 allows an implant to be inserted simultaneously with the desired navigated screw 430 without needing a k-wire 448. In addition, the captured washer 471 can be assembled and disassembled to the head of the navigated screw 430, providing the surgeon with flexibility when using the desired captured washer 471. The captured washer 471 is designed to have two shapes, circular washer 476 and oval washer 474. The circular washer 471 is designed to fit through the end effector 112 while providing the most surface area to displace the load of the implant, preventing navigated screw 430 pull-through or subsidence. The oval washer 474 is designed to fit through the end effector 112 but is ovular in shape to allow the screw heads to be closer together than the circular washer. The oval washer 474 also increases the surface area of an implant to prevent pull-through or subsidence.

The captured washer 471, shown in greater detail in FIG. 27, has an internal spherical radius 504 designed to contour to the head of the navigated screw 430, allowing an implant to rotate about the center of the head of the navigated screw 430. The height 506 of the captured washer 471 is designed to terminate at the top of the head of the navigated screw 430, not to increase soft tissue irritation. In addition, there are flexural grooves 502 that are designed to flex around the head of the navigated screw 430 but spring back to shape to capture the navigated screw 430.

Figure 28:
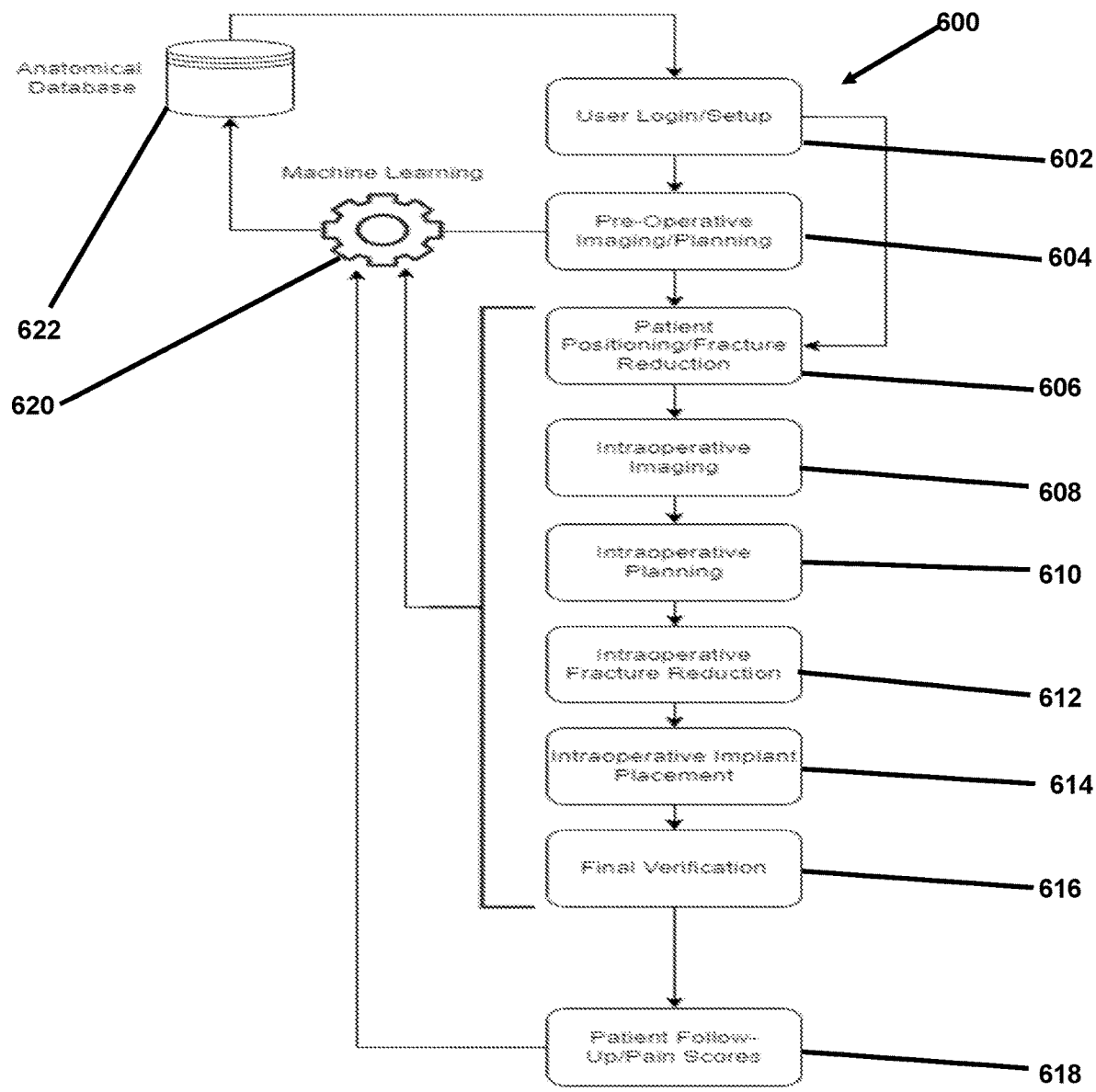
FIG. 28 is a flowchart of the workflow process associated with the present invention.

The workflow of the present invention is shown in FIG. 28 and is generally indicated by the numeral 600. Each workflow step is indicated by numerals <nnn>. The first step in the process is the previously described user login and setup step <602>. As referenced again in FIG. 3, an illustrative but nonlimiting, login screen for the technical specialist of the healthcare facility, e.g., scrub technologist, or a technical specialist from the supplier of the surgical robotic system 100, is generally indicated by numeral 220. This includes a place to enter login information 230, a keyboard to type in login information 232, and a cancel function 234. This can include any type of electronic display, such as that shown by the numeral 110 in FIG. 2.

The next step is to conduct preoperative imaging and planning <604>. This step includes the previously referenced planning and measuring for fracture reduction, planning navigated screw trajectories, and planning implant size and placement, in addition to verifying and finalizing what the surgeon has planned. If this work is already completed, the surgeon can skip from the user login/setup step <602> directly to the next step of patient positioning and fracture reduction <606>. Patient positioning and reduction are equally important to the implant used to treat the associated injury. Failure to reduce the associated injury back to an acceptable level of alignment will have further complications intraoperatively and postoperatively. Once the surgeon is ready to treat the patient, several patient positions and reduction techniques are used to treat various injuries and/or fracture patterns. One technique utilizes external fixation devices that reduce or position the associated injury back to its anatomical position. These devices are usually placed on quickly and directly prior to surgery for a determined amount of time or until the swelling of the soft tissue comes to a viable state suitable for surgery. Because of how quickly these external fixation devices are placed, the accuracy of placement and reduction is sacrificed, which can cause visual and performance complications during surgery. This surgical robotic system 100 can introduce an external fixation device that will be robotically assisted on the placement and provide feedback to the surgeon on how well the associated injury is reduced back to anatomical alignment.

An open reduction internal fixation (ORIF) requires the surgeon to incise and expose the associated injury; however, these incisions must be made into specific anatomical areas due to the risk associated with critical arteries/veins, and reproductive, and digestive anatomy. In addition, if an external fixation device was previously placed before surgery, this could be impeding the associated exposure area or malpositioning the associated injury.

Percutaneous Fixation is typically done through the use of using cannulated or cortex (solid) screws. These screws can vary in diameter, material, and tip geometry in order to achieve the required stability once inserted into boney anatomy. A surgeon typically places these screws in anatomical landmarks on the ilium, pubic, and ischium. The surgeon can then manipulate these screws by translation and rotation to reduce the patient's anatomy into natural alignment.

The next step <608> is that once the patient is positioned, the surgeon will then proceed with obtaining imaging of the patient; this can include but is not limited to, the following modalities: fluoroscopy; CT; MRI; ultrasound; and nuclear medicine Imaging including positron-emission tomography (PET).

After the patient is positioned and the preferred imaging modality has been completed, the surgeon can proceed to intraoperative planning as step <610>. If the surgeon has previously planned the procedure outlined in step <604>, then those trajectories and implant positions can be imported and used. However, if the surgeon requires the need to conduct intraoperative planning, the surgeon will proceed similarly as outlined in the preoperative planning step <604>, without the need to export the data.

Once the surgeon has planned the trajectories and desired outcomes of the associated injury, they can then proceed to the intraoperative reduction of the associated fracture/s and/or injury/s back to their anatomical alignment in step <612>. This workflow step will be the same as described in step <606>.

Once the associated fracture/s and injury/s are reduced to their desired anatomical location and orientation, the surgeon can proceed to implant selection and placement in step <614>. If the surgeon has previously planned the implants via the preoperative workflow in step <604>, this will be implemented utilizing the already planned implants.

After the surgeon has placed all implants, the surgical robotic system 100 will indicate to the surgeon how well the associated injury is reduced back to anatomical alignment as a final verification step <616>. The surgeon will then have to option to make any adjustments needed to meet the desired outcomes. Once no further adjustments are needed, the surgeon will then save and export the patient's file.

Steps <604>, <606>, <607>, <610>, <612>, <614>, and <616> individually or after step <616> can provide input to a machine learning function <620>, which is part of the surgical robotic system 100 will then extrapolate the data to enhance further desired outcomes based off the anatomical data and the implants associated with the patient's file. This will then be sent to the anatomical database <622>. This anatomical database includes both data from specimens that are imaged to provide the database with anatomical data as well as process data in which key anatomical landmarks and characteristics are measured. As this data is continuously entered into the database, machine learning processes this information and segments the data into various patient groups based on age, sex, ethnicity, BMI, and measurements of anatomical landmarks and characteristics. This data will then provide the system with an average of those measured anatomical landmarks and characteristics, based on those segmented patient groups. The surgeon can access this database <622> upon login in step <602>.

The final step is to follow up with the patient at a pre-determined amount of time <618>. During this follow-up, the surgeon or other healthcare provider will then ask the patient a series of questions and or conduct a physical examination. These questions and examination will have an associated score attributed to desired outcomes and an overall score to determine if the surgery successfully achieved these outcomes. Once the questions/examination has been conducted, the data will be analyzed by machine learning <620> and sent to the anatomical database <622>. For example, suppose the patients' scores meet the desired outcome. In that case, the machine learning <620> will then suggest similar trajectories, sizes, and locations of the implants to future patients who present similar attributes as this patient. On the other hand, suppose the patient's pain scores are less than desirable. In that case, machine learning <620> will then take this into account before suggesting similar trajectories, implant size, location, and placement to future patients who present similar anatomical characteristics and fractures/injuries.

From the preceding, it can be seen that the present invention accomplishes at least all of the stated objectives.

Glossary

Unless defined otherwise, all technical and scientific terms used above have the same meaning as commonly understood by one of ordinary skill in the art to which embodiments of the present invention pertain.

The terms "a," "an," and "the" include both singular and plural referents.

The term "or" is synonymous with "and/or" and means any one member or combination of members of a particular list.

The terms "invention" or "present invention" are not intended to refer to any single embodiment of the particular invention but encompass all possible embodiments as described in the specification and the claims.

The term "about" as used herein refer to slight variations in numerical quantities with respect to any quantifiable variable. An inadvertent error can occur, for example, through the use of typical measuring techniques or equipment or from differences in the manufacture, source, or purity of components.

The term "substantially" refers to a great or significant extent. "Substantially" can thus refer to a plurality, majority, and/or a supermajority of said quantifiable variable, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

The "scope" of the present invention is defined by the appended claims, along with the full scope of equivalents to which such claims are entitled. The scope of the invention is further qualified as including any possible modification to any of the aspects and/or embodiments disclosed herein which would result in other embodiments, combinations, subcombinations, or the like that would be obvious to those skilled in the art.

What is claimed is:

1. A navigated pelvic implant system, comprising:
   a robot having a control unit having at least one processor, and an end effector;
   at least one patient position sensor in electronic communication with the robot; and
   a database of anatomical information, including anatomical features, that is in electronic communication with the control unit, wherein the control unit receives patient imaging information and determines variance between a patient and other patients found in the database of anatomical information, and then the control unit selects at least one implant and an associated trajectory for surgery, then the control unit determines position of the patient through input imaging data and input from the at least one patient position sensor, the control unit will then proceed with the previously determined implant and trajectory, unless alteration is required, which is followed by the end effector selectively holding a drill to create an opening in a patient's pelvis along the trajectory that is then followed by the end effector selectively holding an implant insertion mechanism to secure the implant within the opening in the patient's pelvis.

2. The navigated pelvic implant system according to claim 1, wherein the implant insertion mechanism is a driver array, and the implant is a screw.

3. The navigated pelvic implant system according to claim 1, wherein the database of anatomical information includes fracture patterns and fracture level severity to compare a patient against a larger group of patients.

4. The navigated pelvic implant system according to claim 1, wherein the determination of the position of the patient includes a CT scan with at least one reference device selected from the group consisting of a surveillance marker, a bone anchor, a dynamic reference base array, an interoperative CT registration fixture, and a fluoro fixture.

5. The navigated pelvic implant system according to claim 1, wherein the determination of the position of the patient includes a CT scan with at least two reference devices selected from the group consisting of a surveillance marker, a bone anchor, a dynamic reference base array, an interoperative CT registration fixture, and a fluoro fixture.

6. The navigated pelvic implant system according to claim 1, further comprises utilizing a soft tissue sleeve and trocar with the end effector of the robot to perform soft tissue dilation prior to drilling.

7. The navigated pelvic implant system according to claim 1, further comprises utilizing at least one cannula with the end effector of the robot to perform soft tissue dilation prior to drilling.

8. The navigated pelvic implant system according to claim 7, further comprises inserting wire with the end effector of the robot followed by removal of the at least one cannula prior to placement of an implant insertion mechanism to secure an implant in a patient's pelvis.

9. The navigated pelvic implant system, according to claim 1, wherein the drill array includes a threaded sleeve having a geometrically shaped end portion for engagement into a screw.

10. The navigated pelvic implant system according to claim 9, wherein the geometrically shaped end portion of the driver array is hexalobular.

11. The navigated pelvic implant system according to claim 1, wherein the drill array includes a collet sleeve positioned over a collet securing a geometrically shaped end portion for engagement into a screw.

12. The navigated pelvic implant system according to claim 2, wherein the screw includes a threaded connection and geometrically shaped top portion.

13. The navigated pelvic implant system according to claim 12, wherein the geometrically shaped top portion of the screw is hexalobular.

14. The navigated pelvic implant system according to claim 13, wherein the screw includes bone interlocking geometry with an undercut on both the top and bottom of the flutes of the screw.

15. The navigated pelvic implant system according to claim 2, further comprises a captured washer utilized with the screw, wherein the captured washer includes flexural grooves to secure the screw.

16. A navigated pelvic implant system, comprising:
    a robot having a control unit having at least one processor, and an end effector;
    at least one patient position sensor in electronic communication with the robot; and
    a database of anatomical information, including anatomical features, that is in electronic communication with the control unit; wherein the control unit receives patient imaging information and determines variance between a patient and other patients found in the database of anatomical information, then the control unit selects at least one screw and an associated trajectory for surgery, then the control unit determines position of the patient through input imaging data and input from the at least one patient position sensor, the control unit will then proceed with the previously determined screw and trajectory after verification by the control unit, unless alteration is required, which is followed by the end effector selectively holding a drill to create an opening in a patient's pelvis along the trajectory that is then followed by the end effector selectively holding a driver that secures the screw within the opening in the patient's pelvis in accordance with reduction techniques followed by the control system providing surgical procedure verification and providing input into the control system for adjustments to the surgical procedure.

17. The navigated pelvic implant system according to claim 16, further comprises inputting patient procedure and pain information into the control system after the surgical procedure.

18. A method of providing navigated pelvic implants, comprising:
    receiving patient imaging information and determining variance between a patient and other patients in a database of anatomical information, including anatomical features, that is in electronic communication with a control unit, having at least one processor, for a robot having an end effector;
    selecting at least one implant and an associated trajectory for surgery with the control unit;

determining a position of a patient through input imaging data and input from at least one patient position sensor in electronic communication with the control unit;

implementing the previously selected implant and trajectory, unless alteration is required;

selectively holding a drill to create an opening in the patient's pelvis along the trajectory with the end effector; and selectively holding an implant insertion mechanism to secure the implant within the opening in the patient's pelvis with the end effector.

19. The method of providing navigated pelvic implants according to claim 18, wherein the implant insertion mechanism is a driver array, and the implant is a screw.

20. The method of providing navigated pelvic implants according to claim 18, further comprises:

utilizing at least one cannula with the end effector of the robot to perform soft tissue dilation prior to drilling; and inserting wire with the end effector of the robot followed by removal of the at least one cannula prior to placement of an implant insertion mechanism to secure an implant in a patient's pelvis.

* * * * *